United States Patent
Kuduk et al.

(10) Patent No.: US 8,940,765 B2
(45) Date of Patent: Jan. 27, 2015

(54) N-LINKED QUINOLINEAMIDE M1 RECEPTOR POSITIVE ALLOSTERIC MODULATORS

(75) Inventors: Scott D. Kuduk, Harleysville, PA (US); Christina Ng DiMarco, Conshohocken, PA (US); Zhi-Qiang Yang, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/117,265

(22) PCT Filed: May 11, 2012

(86) PCT No.: PCT/US2012/037409
§ 371 (c)(1),
(2), (4) Date: Nov. 12, 2013

(87) PCT Pub. No.: WO2012/158474
PCT Pub. Date: Nov. 22, 2012

(65) Prior Publication Data
US 2014/0200222 A1    Jul. 17, 2014

Related U.S. Application Data

(60) Provisional application No. 61/487,054, filed on May 17, 2011.

(51) Int. Cl.
| C07D 401/14 | (2006.01) |
| A61K 31/04 | (2006.01) |
| C07D 405/14 | (2006.01) |
| C07D 401/06 | (2006.01) |
| C07D 401/12 | (2006.01) |

(52) U.S. Cl.
CPC ............ *C07D 405/14* (2013.01); *C07D 401/06* (2013.01); *C07D 401/14* (2013.01); *C07D 401/12* (2013.01)
USPC .......................................... 514/314; 546/169

(58) Field of Classification Search
USPC .......................................... 514/314; 546/169
See application file for complete search history.

(56) References Cited

U.S. PATENT DOCUMENTS

| 2005/0096312 A1 | 5/2005 | Haeberlein et al. |
| 2006/0079553 A1 | 4/2006 | Hargreaves et al. |

FOREIGN PATENT DOCUMENTS

| WO | WO0073283 | 12/2000 |
| WO | WO2004073639 | 9/2004 |
| WO | WO2005030188 | 4/2005 |
| WO | WO2005056552 | 6/2005 |
| WO | WO2007067489 | 6/2007 |
| WO | 2011/084368 | * 7/2011 |
| WO | WO2011084368 | 7/2011 |

OTHER PUBLICATIONS

Abraham Fisher, Therapeutic Strategies in Alzheimer's Disease: M1 Muscarinic Agonists, Jpn. J. Pharmacol., 2000, pp. 101-112, 84.
Birdsall, Multiple Allosteric Sites on Muscarinic Receptors, NPL—Birdsall—2001-2517, 2001, 2517-2524, 58, Life Science.
Brauner-Osborne, Pharmacology of Muscarinic Acetylcholine Receptor Subtypes (m1-m5): High Throughout Assays in Mammalian Cells, E. Journal of Pharmacology, 1996, 93-102, 295.
Christopoulos, Allosteric Binding Sites on Cell-Surface Receptors: Novel Targets for Drug Discovery, Nature, 2002, 198-210, 1.
Eglen, Therapeutic Opportunties from Muscarinic Receptor Research, Trends in Pharmacological Sciences, Aug. 2001, 409-414, 8.
Lazareno, Analogs of WIN 62,577 Define a Second Allsoteric Site on Muscarinic Receptors, Molecular Pharmacology, 2002, 1492-1505, 62.
Lazereno, Allosteric Interactions of Staurosporine and Other Indolocarbazoles with N-[Methyl-3H]Scopolamine and Acetylcholine at Muscarinic Receptor Subtypes: Identification of a Second Allosteric Site, Molecular Pharmacology, Mar. 22, 2000, 194-207, 58.
Spalding et al., Discovery of an Ectopic Activation Site on the M1 Muscarinic Receptor, Site on the M1 Muscarinic Receptor, 2002, pp. 1297-1302, 61, Molecular Pharmacology, US.

* cited by examiner

*Primary Examiner* — D M Seaman
(74) *Attorney, Agent, or Firm* — Sylvia A. Ayler; John C. Todaro

(57) ABSTRACT

The present invention is directed to N-linked quinoline amide compounds of general formula (I) which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

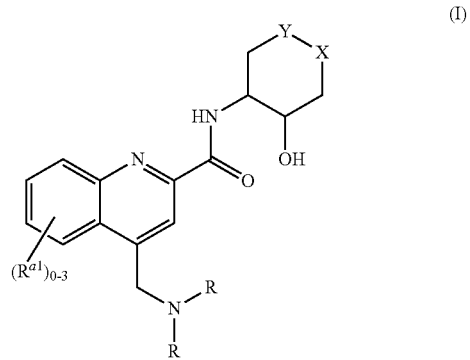

15 Claims, No Drawings

N-LINKED QUINOLINEAMIDE M1 RECEPTOR POSITIVE ALLOSTERIC MODULATORS

CROSS REFERENCE TO RELATED APPLICATIONS

This application is a 371 of International Application No. PCT/US2012/037409 filed on May 11, 2012, which claims the benefit under 35 U.S.C. 119(e) of U.S. Provisional Application No. 61/487,054, filed May 17, 2011.

FIELD OF THE INVENTION

The invention is directed to a class of N-linked quinoline amide compounds, their salts, pharmaceutical compositions comprising them and their use in therapy of the human body. In particular, the invention is directed to a class of N-linked quinoline amide compounds which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences*, 2001, 22:8, 409-414.

In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacol*, 2000, 84:101-112.

However, M1 ligands which have been developed and studied for Alzheimer's Disease have produced side effects common to other muscarinic receptor ligands, such as sweating, nausea and diarrhea. See Spalding et al, *Mol Pharmacol*, 2002, 61:6, 1297-1302. See also WO2005056552, WO2005030188 and WO2007067489.

The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505; S. Lazareno et al, *Mol Pharmacol*, 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is directed to novel N-linked quinoline amide compounds of generic formula (I) described below, or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to N-linked quinoline amide compounds of general formula (I)

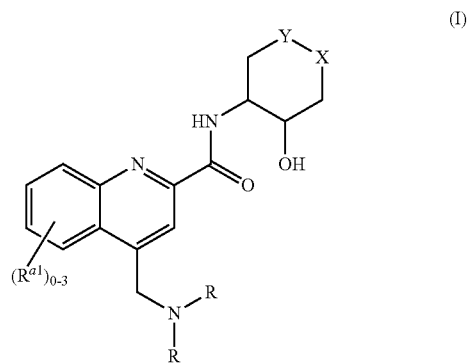

(I)

and pharmaceutically acceptable salts thereof, wherein X=Y=CH$_2$, X=O and Y=CH$_2$, or X=CH$_2$ and Y=O; each R is selected from the group consisting of
(1) hydrogen,
(2) C$_{6-10}$ aryl,
(3) C$_{5-10}$ heterocycle, optionally substituted with 1 to 3 groups of R$^a$,
(4) —C$_{1-6}$ alkyl, optionally substituted with 1 to 3 groups of R$^a$,
(5) —C$_{2-6}$ alkenyl, optionally substituted with 1 to 3 groups of R$^a$,
(6) —S(=O)$_n$—R$^1$,
(7) —OH,
(8) or R and R can be linked together with the nitrogen to which they are both attached to form a 3-6 membered heterocyclic ring, wherein one or two of the ring carbon atoms are optionally replaced by a nitrogen, oxygen or sulfur; wherein said heterocyclic ring is optionally susbstituted with 1 to 3 groups of R$^a$, R$^a$ and R$^{a1}$ are independently selected from the group consisting of:
(1) hydroxyl,
(2) halogen,
(3) C$_{1-6}$alkyl,
(4) C$_{6-10}$aryl, which is unsubstituted or substituted with 1 to 3 groups of R$^b$,
(5) (CH$_2$)$_n$C$_{5-10}$heterocyclyl, which is unsubstituted or substituted with 1 to 3 groups of R$^b$, and
(6) —CN, R$^b$ is selected from the group consisting of:
(1) hydroxyl,
(2) halogen,
(3) C$_{1-6}$alkyl, and
(4) C$_{1-4}$ haloalkyl, R$^1$ is selected from the group consisting of:
(1) hydrogen,
(2) —C$_{1-6}$ alkyl,
(3) —C$_{2-6}$ alkenyl, and
(4) —N(R$^1$)$_2$ n is 0-4.

In one embodiment of the compounds of formula (I) X=O and Y=CH$_2$, and all other variables are as originally described.

In another embodiment of the compounds of formula (I) X=CH$_2$, and Y=O and all other variables are as originally described.

In another embodiment of the compounds of formula (I) X=Y=CH$_2$, and all other variables are as originally described.

In another embodiment of the compounds of formula (I) R and R are linked together with the nitrogen to which they are both attached to form a 3-6 membered heterocyclic ring, wherein one or two of the ring carbon atoms is optionally replaced by a nitrogen, oxygen or sulfur; and wherein said heterocyclic ring is optionally susbstituted with 1 to 3 groups of R$^a$. A subembodiment of this aspect of the invention is realized when the heterocyclic ring formed by linking R and R is substituted with 0 to 2 groups of R$^a$, preferably 2. Another subembodiment of this aspect of the invention is realized when the heterocyclic ring is piperidinyl or piperazinyl. Still another subembodiment of this aspect of the invention is realized when the heterocyclic ring is piperidinyl. Yet another subembodiment of this aspect of the invention is realized when the heterocyclic ring is piperazinyl.

In another embodiment of the compounds of formula (I) R$^{a1}$ is absent.

In still another embodiment of the compounds of formula (I) one R$^{a1}$ is present and is halogen, preferably fluorine.

In another embodiment of the compounds of formula (I) two R$^{a1}$ are present and are halogen, preferably fluorine.

In another embodiment of the compounds of formula (I) R$^a$ is C$_{1-6}$alkyl and all other variables are as originally described.

In another embodiment of the compounds of formula (I) R$^a$ is halogen and all other variables are as originally described.

In another embodiment of the compounds of formula (I) R$^a$ is CN and all other variables are as originally described.

In another embodiment of the compounds of formula (I) R$^a$ is C$_{6-10}$aryl, which is unsubstituted or substituted with 1 to 3 groups of R$^b$, and all other variables are as originally described. A subembodiment of this aspect of the invention is realized when R$^a$ is optionally substituted phenyl.

In another embodiment of the compounds of formula (I) R$^a$ is C$_{5-10}$heterocyclyl, which is unsubstituted or substituted with 1 to 3 groups of R$^b$, and all other variables are as originally described. A subembodiment of this aspect of the invention is realized when R$^a$ is optionally substituted pyridyl, pyrazolyl, pyrazinyl, pyrimidinyl and pyradazinyl.

In another embodiment of the compounds of formula (I) R$^b$ is selected from the group consisting of methyl, ethyl, propyl, butyl, halo, and CF$_3$.

Still another embodiment of the compounds of formula (I) is represented by structural formula Ia:

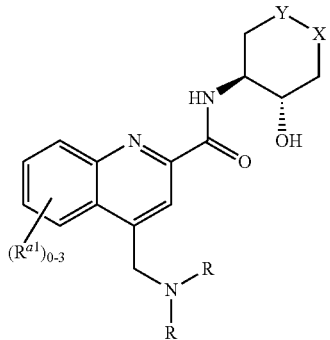

Ia or a pharmaceutically acceptable salt thereof wherein X, Y, R$^{a1}$, and R are as originally described. A subembodiment of this invention is realized when R and R are linked together with the nitrogen to which they are both attached to form a 3-6 membered heterocyclic ring, wherein one or two of the ring carbon atoms is optionally replaced by a nitrogen, oxygen or sulfur; and wherein said heterocyclic ring is optionally susbstituted with 1 to 3 groups of R$^a$. A subembodiment of this aspect of the invention is realized when the heterocyclic ring formed by linking R and R is substituted with 1 to 2 groups of R$^a$.

Another embodiment of the compounds of formula (I) is represented by structural formula Ib:

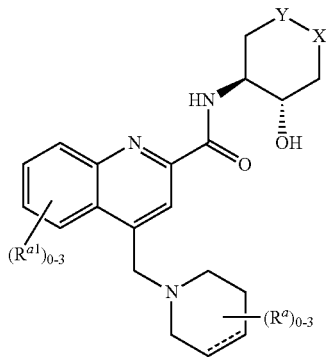

or a pharmaceutically acceptable salt thereof wherein X, Y, $R^{a1}$ and $R^a$ are as originally described and - - - represents a bond that is present or absent. A subembodiment of formula Ib is realized when X=Y=CH$_2$ or X=O and Y=CH$_2$. Another subembodiment of formula Ib is realized when - - - is absent. Another subembodiment of formula Ib is realized when - - - is present. Still another subembodiment of formula Ib is realized when $R^a$ is in the 4 position with respect to the nitrogen. Yet another subembodiment of formula Ib is realized when $R^a$ is selected from the group consisting of CN, halo, and optionally substituted phenyl, pyridyl, pyrazolyl, pyrazinyl, pyrimidinyl and pyradazinyl. Another subembodiment of formula Ib is realized when - - - is absent, X=Y=CH$_2$, $R^a$ is in the 4 position and selected from the group consisting of CN, halo, and optionally substituted phenyl, pyridyl, pyrazolyl, pyrazinyl, pyrimidinyl and pyradazinyl.

Another embodiment of the compounds of formula (I) is represented by structural formula Ic:

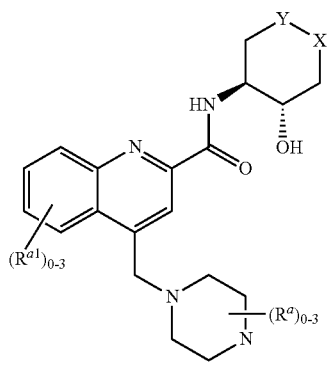

or a pharmaceutically acceptable salt thereof wherein X, Y, $R^{a1}$ and $R^a$ are as originally described. A subembodiment of formula Ic is realized when X=Y=CH$_2$ or X=O and Y=CH$_2$. Yet another subembodiment of formula Ic is realized when $R^a$ is selected from the group consisting of CN, halo, and optionally substituted phenyl, pyridyl, pyrazolyl, pyrazinyl, pyrimidinyl and pyradazinyl. Still another subembodiment of formula Ic is realized when X=Y=CH$_2$, $R^a$ is selected from the group consisting of CN, halo, and optionally substituted phenyl, pyridyl, pyrazolyl, pyrazinyl, pyrimidinyl and pyradazinyl.

Specific examples of the compounds of formula (I) are:
4-[(4-cyano-4-pyridin-2-ylpiperidin-1-yl)methyl]-N-[(1S,2S)-2-hydroxycyclohexyl]quinoline-2-carboxamide,
N-[(1S,2S)-2-hydroxycyclohexyl]-4-{[4-(1-methyl-1H-pyrazol-4-yl)piperazin-1-yl]methyl}quinoline-2-,
4-{[4-cyano-4-(4-methylpyridin-2-yl)piperidin-1-yl]methyl}-N-[(1S,2S)-2-hydroxycyclohexyl]quinoline-2-carboxamide,
4-[(4-cyano-4-phenylpiperidin-1-yl)methyl]-N-[(1S,2S)-2-hydroxycyclohexyl]quinoline-2-carboxamide,
4-{[4-cyano-4-(2-fluorophenyl)piperidin-1-yl]methyl}-N-[(1S,2S)-2-hydroxycyclohexyl]quinoline-2-carboxamide,
4-{[4-(2-chlorophenyl)-4-cyanopiperidin-1-yl]methyl}-N-[(1S,2S)-2-hydroxycyclohexyl]quinoline-2-carboxamide,
4-{[4-cyano-4-(2-methylphenyl)piperidin-1-yl]methyl}-N-[(1S,2S)-2-hydroxycyclohexyl]quinoline-2-carboxamide,
1,5-anhydro-3-{[(4-{[4-cyano-4-(4-methylpyridin-2-yl)piperidin-1-yl]methyl}quinolin-2-yl)carbonyl]amino}-2,3-dideoxy-L-threo-pentitol,
4-[(4-cyano-4-pyridin-3-ylpiperidin-1-yl)methyl]-N-[(1S,2S)-2-hydroxycyclohexyl]quinoline-2-carboxamide,
4-[(4-cyano-4-pyridin-4-ylpiperidin-1-yl)methyl]-N-[(1S,2S)-2-hydroxycyclohexyl]quinoline-2-carboxamide,
8-fluoro-4-[(4-fluoro-4-phenylpiperidin-1-yl)methyl]-N-[(1S,2S)-2-hydroxycyclohexyl]quinoline-2-carboxamide,
1,5-anhydro-2,3-dideoxy-3-[({8-fluoro-4-[(4-fluoro-4-phenylpiperidin-1-yl)methyl]quinolin-2-yl}carbonyl)amino]-L-threo-pentitol,
8-fluoro-N-[(1S,2S)-2-hydroxycyclohexyl]-4-{[4-(1-methyl-1H-pyrazol-4-yl)piperazin-1-yl]methyl}quinoline-2-carboxamide,
4-[(4-cyano-4-pyrazin-2-ylpiperidin-1-yl)methyl]-8-fluoro-N-[(1S,2S)-2-hydroxycyclohexyl]quinoline-2-carboxamide,
4-[(4-cyano-4-pyrimidin-4-ylpiperidin-1-yl)methyl]-8-fluoro-N-[(1S,2S)-2-hydroxycyclohexyl]quinoline-2-carboxamide,
8-fluoro-4-[(4-fluoro-4-pyridin-2-ylpiperidin-1-yl)methyl]-N-[(1S,2S)-2-hydroxycyclohexyl]quinoline-2-carboxamide,
4-[(4-cyano-4-pyridazin-4-ylpiperidin-1-yl)methyl]-8-fluoro-N-[(1S,2S)-2-hydroxycyclohexyl]quinoline-2-carboxamide,
4-(3',6'-dihydro-2,4'-bipyridin-1'(2'N-ylmethyl)-8-fluoro-N-[(1S,2S)-2-hydroxycyclohexyl]quinoline-2-carboxamide,
8-fluoro-N-[(1S,2S)-2-hydroxycyclohexyl]-4-({4-[4-(trifluoromethyl)phenyl]piperidin-1-yl}methyl)quinoline-2-carboxamide,
8-fluoro-N-[(1S,2S)-2-hydroxycyclohexyl]-4-[(4-pyridin-4-ylpiperidin-1-yl)methyl]quinoline-2-carboxamide,
8-fluoro-N-[(1S,2S)-2-hydroxycyclohexyl]-4-[(4-phenylpiperidin-1-yl)methyl]quinoline-2-carboxamide,
4-[(4-cyano-4-pyridin-4-ylpiperidin-1-yl)methyl]-8-fluoro-N-[(1S,2S)-2-hydroxycyclohexyl]quinoline-2-carboxamide,
8-fluoro-N-[(1S,2S)-2-hydroxycyclohexyl]-4-[(4-pyridin-3-ylpiperidin-1-yl)methyl]quinoline-2-carboxamide,
4-[(4-cyano-4-pyridin-3-ylpiperidin-1-yl)methyl]-8-fluoro-N-[(1S,2S)-2-hydroxycyclohexyl]quinoline-2-carboxamide,
8-fluoro-N-[(1S,2S)-2-hydroxycyclohexyl]-4-[(4-pyridin-2-ylpiperidin-1-yl)methyl]quinoline-2-carboxamide,
4-[(4-cyano-4-fluoropiperidin-1-yl)methyl]-8-fluoro-N-[(1S,2S)-2-hydroxycyclohexyl]quinoline-2-carboxamide,
4-[(4-cyano-4-fluoropiperidin-1-yl)methyl]-5,8-difluoro-N-[(1S,2S)-2-hydroxycyclohexyl]quinoline-2-carboxamide, 4-{[4-cyano-4-(4-methylpyridin-2-yl)piperidin-1-yl]methyl}-8-fluoro-N-[(1S,2S)-2-hydroxycyclohexyl]quinoline-2-carboxamide, 4-{[4-cyano-4-(4-methylpyridin-2-yl)piperidin-1-yl]methyl}-5,8-difluoro-N-[(1S,2S)-2-hydroxycyclohexyl] quinoline-2-carboxamide, 4-{[4-(4-chloropyridin-2-yl)-4-fluoropiperidin-1-yl]methyl}-8-fluoro-N-[(1S,2S)-2-hydroxycyclohexyl]quinoline-2-carboxamide, 8-fluoro-4-{[4-fluoro-4-(4-methylpyridin-2-yl)piperidin-1-yl]methyl}-N-[(1S,2S)-2-hydroxycyclohexyl]quinoline-2-carboxamide, and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formula (I), or a pharmaceutically acceptable salt thereof.

The invention is also directed to the use of a compound of formula (I), for treating a disease or disorder in which the M1 receptor is involved, such as Alzheimer's Disease, cognitive impairment, schizophrenia, pain disorders and sleep disorders, by administering to the patient a compound of formula (I), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formula (I), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formula (I), or a pharmaceutically acceptable salt thereof, with a pharmaceutically acceptable carrier.

When any variable (e.g. aryl, heterocycle, $R^1$, $R^5$ etc.) occurs more than one time in any constituent, its definition on each occurrence is independent at every other occurrence. Also, combinations of substituents and/or variables are permissible only if such combinations result in stable compounds.

If and when $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyl are $C_2$-$C_6$ alkynyl.

"Alkenyl," "alkynyl" and other like terms include carbon chains containing at least one unsaturated C—C bond.

As used herein, "fluoroalkyl" refers to an alkyl substituent as described herein containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

In certain other embodiments, the heterocyclic group is fused to an aryl or heteroaryl group. Examples of such fused heterocycles include, without limitation, tetrahydroquinolinyl and dihydrobenzofuranyl.

The term "heterocycloalkyl", as used herein except where noted, represents a non-aromatic cyclic or polycyclic group having from five to twelve ring atoms selected from C, O, N or S, at least one of which is O, N or S. Examples of heterocycloalkyls include azetidinyl, pyrrolidinyl, piperidinyl, piperazinyl, morpholinyl, pyranyl, tetrahydrofuranyl, imidazolinyl, pyrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2,4-difluoro-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:
  (a) halo, cyano, oxo, carboxy, formyl, nitro, amino, amidino, guanidino, and
  (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" or "halo" refers to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formula (I).

Formula (I), are shown above without a definite stereochemistry. The present invention includes all stereoisomers of formula (I), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

Specific embodiments of the compounds of the invention, and methods of making them, are described in the Examples herein.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

Suitable pharmaceutically acceptable salts include ammonium, sodium, potassium, hydrochloride, hydrobromide and fumarate.

The present invention is directed to the use of the compounds of formula (I) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sun-downing; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists, such as ABT089, SSR180711 and MEM63908; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; $GABA_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B 1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formula (I) is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The following abbreviations are used throughout the text:

Me: methyl
Et: ethyl
t-Bu: tert-butyl
Ar: aryl
Ph: phenyl
Bn: benzyl
DCE: dichloroethylene
HMDS: hexamethyldisilazane
DMF: dimethylformamide
DMFDMA: N,N-dimethylformamide dimethylacetal
THF: tetrahydrofuran
BOP: benzotriazolyloxytris (dimethylamino) phosphonium hexafluorophosphate
Boc: tert-butyloxycarbonyl
TBS: tert-butyldimethylsilyl
TEA: triethylamine
TPAP: tetra-n-propyl ammonium perruthenate
NMO: N-methyl morpholine N-oxide
ClZn: Chlorozinc
dppf: diphenylphosphorousferrocenyl
PMB: p-methoxybenzyl
Ms: mesyl
Ac: acetyl
DMSO: dimethylsulfoxide
DCM: dichloromethane
m-CPBA: meta-chloroperoxybenzoic acid
DMEM: Dulbecco's Modified Eagle Medium (High Glucose)
FBS: fetal bovine serum
rt: room temperature
aq: aqueous
HPLC: high performance liquid chromatography
MS: mass spectrometry
CDX TA P1G5 **
GDH-103 **
KRED-130 **

**Codex Transaminase panel enzyme P1G5 (commercially available from Codex (Redwood City, Calif., USA) panel products.

Several methods for preparing the compounds of this invention are illustrated in the schemes and examples herein. Starting materials are made according to procedures known in the art or as illustrated herein. The following examples are provided so that the invention might be more fully understood. The present invention also provides a method for the synthesis of compounds useful as intermediates in the preparation of compounds of the invention.

In method A, bromoquinoline ester A1 may undergo a cross coupling with a reagent such as vinyl potassium trifluoroborate with a catalyst like palladium to provide A2. Ozonolysis provides aldehyde A3, which can undergo a reductive amination reaction with an amine and a reducing agent such as sodium triacetoxy borohydride to yield A4. Hydrolysis using a base like sodium hydroxide followed by coupling with an amine such as (1S,2S)-2-aminocyclohexanol and a coupling reagent such as benzotriazol-1-yloxy)tris(dimethylamino)phosphonium hexafluorophosphate (BOP) leads to Example A.

Method A

Example A

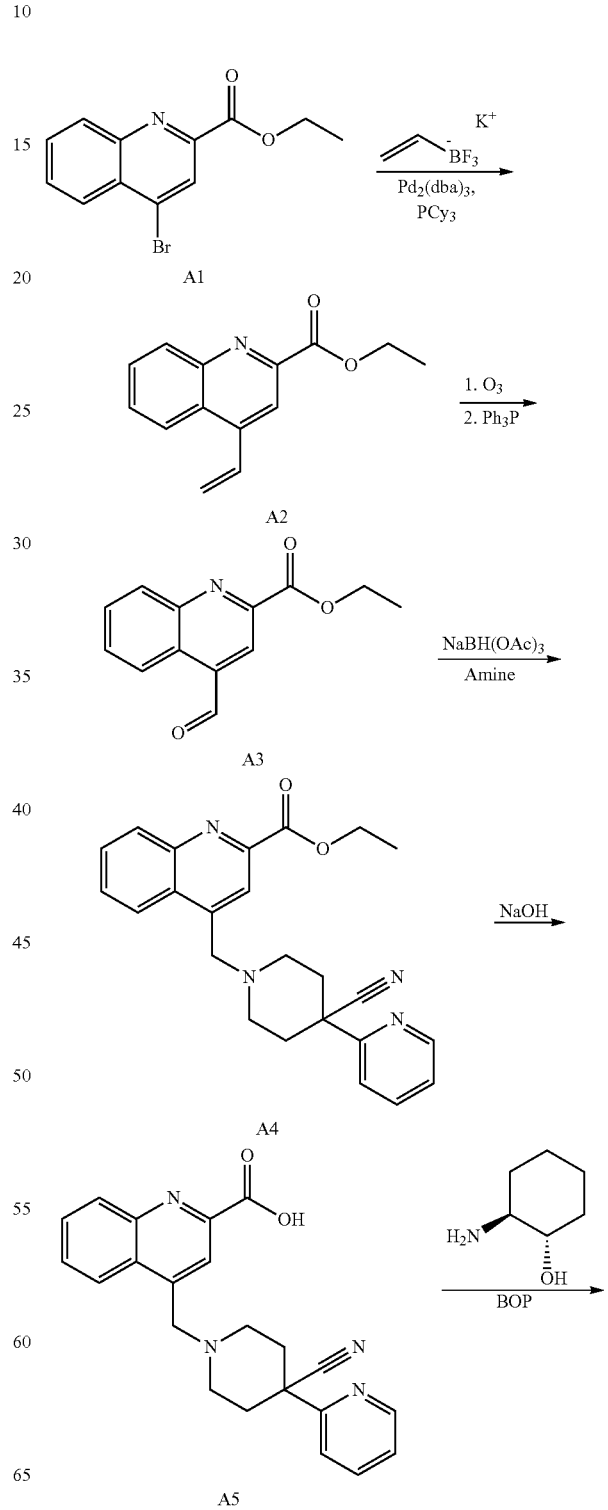

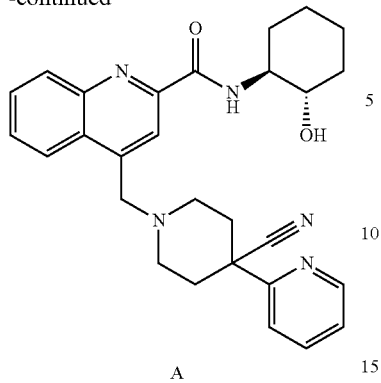

In method B, aldehyde A3 from method A may first undergo hydrolysis to provide B1. Coupling and reductive amination as described previously in method A provides Example B.

Method B

Example B

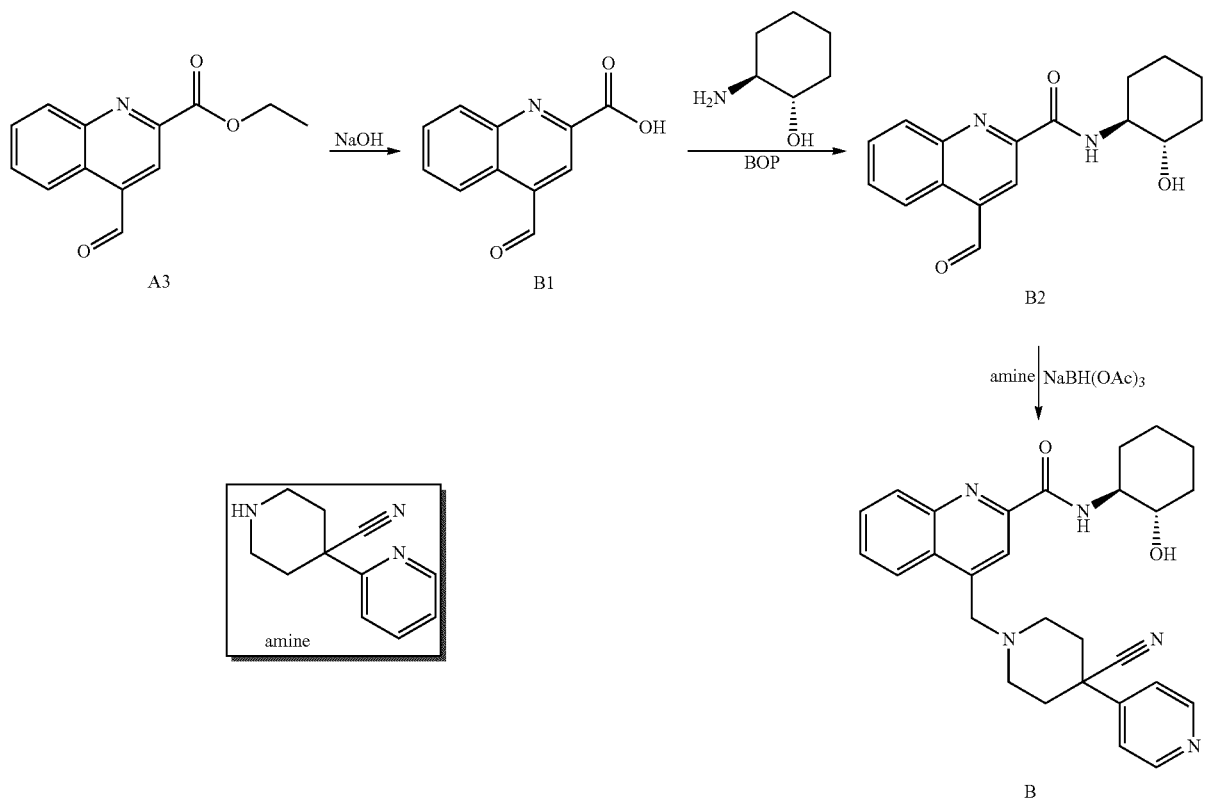

In method C, the amine is constructed via addition of the appropriate organometallic reagent generated from C2 with butyllithium and ketone C1 to provide C3. Treatment of the alcohol in C3 with a fluorinating agent such as deoxofluor provides C4. Removal of the Boc group may be accomplished using an acid such as hydrogen chloride leading to amine C5, which may undergo reductive amination as described in method A to provide Example C. Amine C9 can be obtained in an analogous fashion as shown in method A.

25 26
Method C
Example C
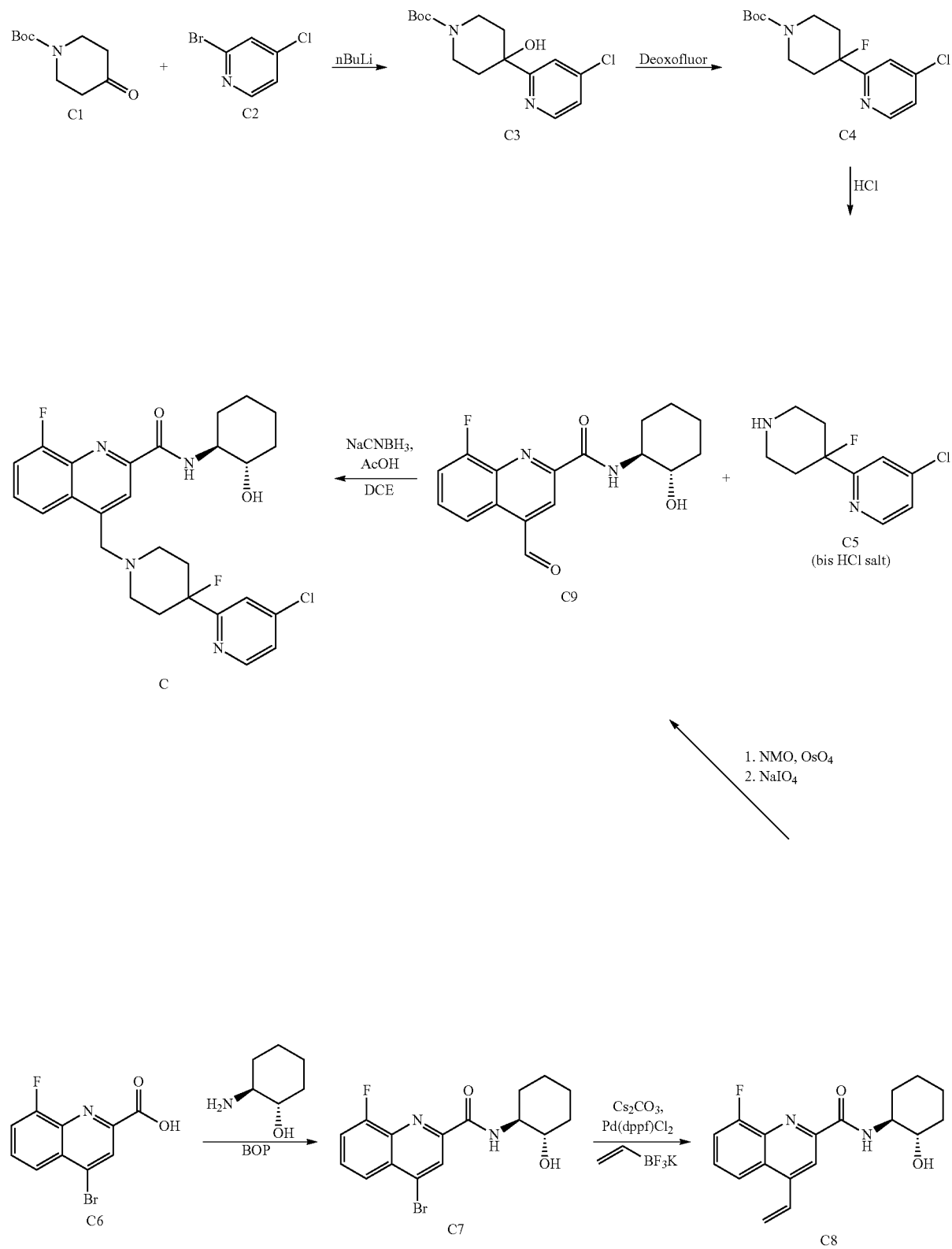

Lastly, in method D, the chloride in Example C may undergo further modification such as conversion to a methyl using an organometallic such as dimethylzinc and a transition metal catalyst like palladium to provide Example D.

Method D

Example D

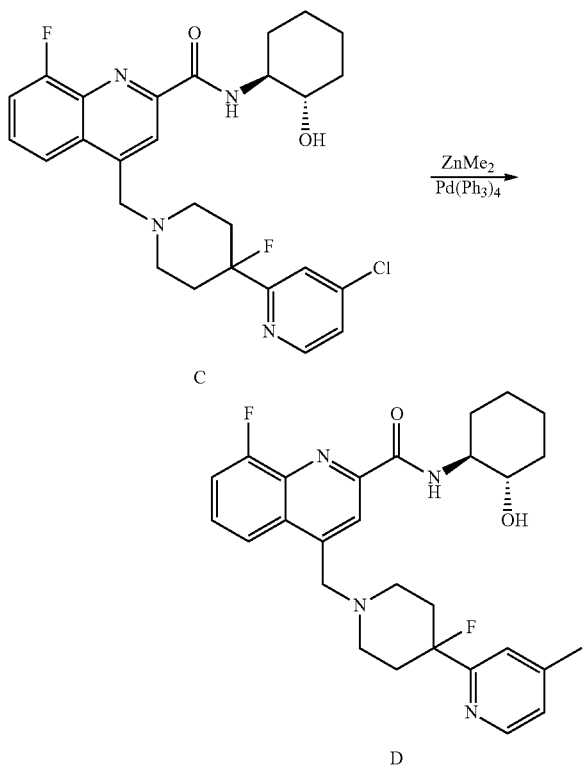

Method A-1

Representative Example A

4-{[4-Cyano-4-(pyridin-2-yl)piperidin-1-yl]methyl}-N-[(1S,2S)-2-hydroxycyclohexyl]quinoline-2-carboxamide

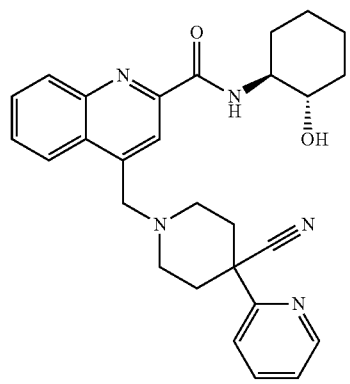 [SMILES: N#CC1(c2ccccn2)CCN(Cc2cc(C(=O)N[C@H]3CCCC[C@@H]3O)nc3ccccc23)CC1]

A solution of ethyl 4-hydroxyquinoline-2-carboxylate (10.0 g, 46.0 mmol) and phosphorus oxybromide (13.2 g, 46.0 mmol) in 100 mL of toluene and 10.0 mL acetonitrile was heated at 75° C. for 1.5 h. The reaction mixture was cooled to room temperature, quenched slowly with water, and extracted with ethyl acetate. The organic fraction was washed with brine, dried over sodium sulfate, filtered, and concentrated. The resultant residue was subjected to silica gel chromatography eluting with 0-50% ethyl acetate in hexanes to afford ethyl 4-bromoquinoline-2-carboxylate that gave a mass ion (ES+) of 280.1 ($^{79}$Br) for M+H$^+$.

In a microwave vial containing the above compound (0.50 g, 1.79 mmol), potassium vinyltrifluoroborate (0.36 mg, 2.68 mmol), Pd$_2$(dba)$_3$ (16 mg, 0.018 mmol), and tricyclohexylphosphine (12 mg, 0.043 mmol) was added 5.9 mL of dioxane and 2.4 mL 1.27 M aqueous tribasic potassium phosphate. The reaction was heated to 140° C. in microwave reactor for 30 minutes. The reaction mixture was extracted with methylene chloride, dried over sodium sulfate, filtered, and concentrated. The resultant residue was subjected to silica gel chromatography eluting with 0-40% ethyl acetate in hexanes to afford ethyl 4-ethenylquinoline-2-carboxylate that gave a mass ion (ES+) of 228.2 for M+H$^+$.

A solution of the above compound (0.18 g, 0.77 mmol) in 3.8 mL methylene chloride was cooled to −78° C. Ozone was bubbled into the reaction mixture for 10 min and then 1.2 g polymer-supported triphenylphosphine was added. The reaction mixture was warmed to room temperature, filtered, washed with excess methanol, and concentrated. The resultant residue was subjected to silica gel chromatography eluting with 0-40% ethyl acetate in hexanes to afford ethyl 4-formylquinoline-2-carboxylate that gave a mass ion (ES+) of 230.2 for M+H$^+$.

To a solution of the above compound (0.050 g, 0.218 mmol) in 0.85 mL dichloroethane was added 4-(pyridin-2-yl)piperidine-4-carbonitrile (0.061 g, 0.327 mmol), and sodium triacetoxyborohydride (0.069 g, 0.327 mmol). The reaction mixture was stirred at room temperature overnight and concentrated. The resultant residue was subjected to purification via reverse phase HPLC to afford ethyl 4-{[4-cyano-4-(pyridin-2-yl)piperidin-1-yl]methyl}quinoline-2-carboxylate that gave a mass ion (ES+) of 401.4 for M+H+.

To a solution of the above compound (0.075 g, 0.187 mmol) in 0.50 mL methanol and 0.05 mL THF was added aqueous 1 N NaOH (0.20 mL, 0.20 mmol). After 1.5 h, the reaction mixture was concentrated to afford sodium 4-{[4-cyano-4-(pyridin-2-yl)piperidin-1-yl]methyl}quinoline-2-carboxylate that gave a mass ion (ES+) of 373.4 for M+H$^+$.

To a solution of the above compound (0.074 g, 0.188 mmol) in 0.50 mL DMF was added (1S,2S)-2-aminocyclohexanol (0.024 g, 0.206 mmol), (benzotriazol-1-yloxy)tris(dimethylamino)phosphonium hexafluorophosphate (BOP) (0.091 g, 0.206 mmol), and triethylamine (0.029 mL, 0.206 mmol). The reaction was stirred at room temperature for 1.5 h. The crude reaction mixture was subjected to purification via reverse phase HPLC to afford 4-{[4-cyano-4-(pyridin-2-yl)piperidin-1-yl]methyl}-N-[(1S,2S)-2-hydroxycyclohexyl]quinoline-2-carboxamide that gave a mass ion (ES+) of 470.2563 for M+H$^+$. $^1$H NMR (400 MHz, CDCl$_3$): δ 8.60 (d, J=4.8 Hz, 1H); 8.36 (s, 1H); 8.30-8.16 (m, 3H); 7.89-7.83 (m, 1H); 7.79-7.72 (m, 2H); 7.49 (d, J=8.0 Hz, 1H); 7.31-7.27 (m, 1H); 4.75 (d, J=9.7 Hz, 2H); 3.94-3.75 (m, 2H); 3.66-3.58 (m, 1H); 3.28 (dd, J=23.3, 11.6 Hz, 3H); 2.79-2.69 (m, 2H); 2.34 (d, J=14.7 Hz, 2H); 2.21-2.06 (m, 2H); 1.85-1.76 (m, 2H); 1.52-1.30 (m, 4H).

The following examples were synthesized using Method A

N-[(1S,2S)-2-hydroxycyclohexyl]-4-{[4-(1-methyl-1H-pyrazol-4-yl)piperazin-1-yl]methyl}quinoline-2-carboxamide

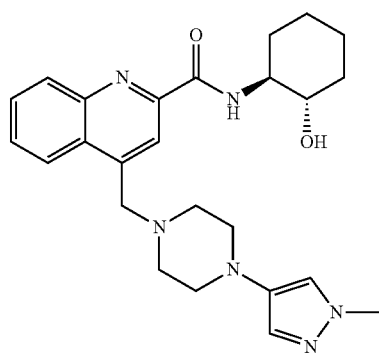 [SMILES: Cn1cc(N2CCN(Cc3cc(C(=O)N[C@H]4CCCC[C@@H]4O)nc4ccccc34)CC2)cn1]

¹H NMR (400 MHz, CDCl₃): δ 8.34 (s, 1H); 8.27-8.22 (m, 2H); 8.18 (d, J=8.4 Hz, 1H); 7.88-7.83 (m, 1H); 7.77-7.72 (m, 1H); 7.24 (d, J=0.9 Hz, 1H); 7.11 (s, 1H); 4.67 (s, 2H); 3.95-3.84 (m, 1H); 3.84 (s, 3H); 3.65-3.56 (m, 1H); 3.29 (d, J=27.2 Hz, 8H); 2.20-2.10 (m, 2H); 1.82 (d, J=11.2 Hz, 2H); 1.54-1.29 (m, 4H). HRMS 449.2678 M+H⁺.

4-{[4-Cyano-4-(4-methylpyridin-2-yl)piperidin-1-yl]methyl}-N-[(1S,2S)-2-hydroxycyclohexyl]quinoline-2-carboxamide

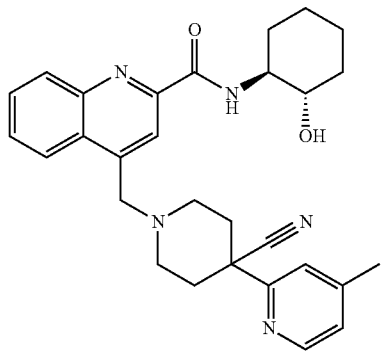

¹H NMR (400 MHz, CDCl₃): δ 8.45 (d, J=5.0 Hz, 1H); 8.36-8.25 (m, 3H); 8.13 (d, J=8.5 Hz, 1H); 7.81-7.73 (m, 1H); 7.67-7.60 (m, 1H); 7.40 (s, 1H); 7.06 (d, J=5.0 Hz, 1H); 4.08 (s, 2H); 3.94-3.83 (m, 1H); 3.61-3.53 (m, 1H); 3.46 (d, J=4.1 Hz, 1H); 3.03 (d, J=11.8 Hz, 2H); 2.74-2.61 (m, 2H); 2.38 (m, 5H); 2.20-2.04 (m, 3H); 1.81 (d, J=11.4 Hz, 2H); 1.55-1.30 (m, 4H).

4-{[4-(2-Chlorophenyl)-4-cyanopiperidin-1-yl]methyl}-N-[(1S,2S)-2-hydroxycyclohexyl]quinoline-2-carboxamide

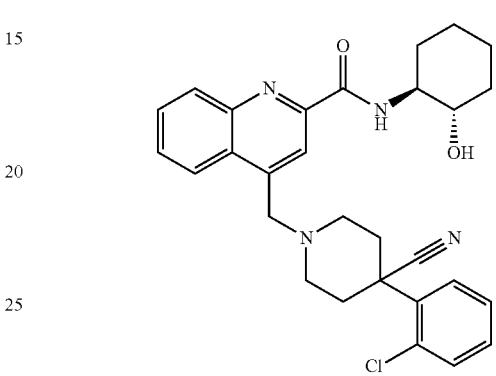

¹H NMR (400 MHz, CDCl₃): δ 8.37 (s, 1H); 8.31-8.22 (m, 2H); 8.14 (d, J=8.5 Hz, 1H); 7.80-7.74 (m, 1H); 7.67-7.61 (m, 1H); 7.48-7.44 (m, 1H); 7.41-7.37 (m, 1H); 7.32-7.27 (m, 2H); 4.11 (s, 2H); 3.91-3.86 (m, 1H); 3.61-3.54 (m, 1H); 3.44 (d, J=4.2 Hz, 1H); 3.06 (d, J=12.0 Hz, 2H); 2.86-2.74 (m, 2H); 2.54 (d, J=12.9 Hz, 2H); 2.20-2.09 (m, 3H); 1.81 (d, J=11.4 Hz, 2H); 1.53-1.33 (m, 4H). FIRMS 503.2217 M+H⁺.

4-{[4-Cyano-4-(2-methylphenyl)piperidin-1-yl]methyl}-N-[(1S,2S)-2-hydroxycyclohexyl]quinoline-2-carboxamide

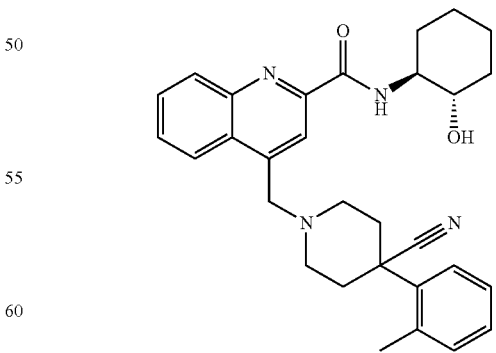

¹H NMR (400 MHz, CDCl₃): δ 8.36 (s, 1H); 8.31-8.24 (m, 2H); 8.14 (d, J=8.5 Hz, 1H); 7.79-7.74 (m, 1H); 7.64 (d, J=1.6 Hz, 1H); 7.26 (s, 3H); 4.11 (s, 2H); 3.94-3.84 (m, 1H); 3.62-3.53 (m, 1H); 3.44 (d, J=4.1 Hz, 1H); 3.05 (d, J=11.9 Hz, 2H);

2.84-2.74 (m, 2H); 2.64 (s, 3H); 2.34 (d, J=13.0 Hz, 2H); 2.18-2.06 (m, 3H); 1.81 (d, J=11.5 Hz, 2H); 1.54-1.30 (m, 4H). HRMS 483.2768 M+H⁺.

1,5-Anhydro-3-{[(4-{[4-cyano-4-(4-methylpyridin-2-yl)piperidin-1-yl]methyl}quinolin-2-yl)carbonyl]amino}-2,3-dideoxy-L-threo-pentitol

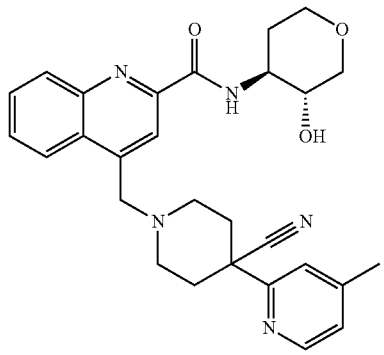 [SMILES: Cc1ccnc(C2(C#N)CCN(Cc3cc(C(=O)N[C@H]4CCOC[C@@H]4O)nc4ccccc34)CC2)c1]

$^1$H NMR (400 MHz, CDCl$_3$): δ 8.45 (d, J=5.0 Hz, 1H); 8.39-8.28 (m, 2H); 8.14 (d, J=8.5 Hz, 1H); 7.79 (ddd, J=8.5, 6.8, 1.4 Hz, 1H); 7.66 (ddd, J=8.5, 6.8, 1.3 Hz, 1H); 7.40 (s, 1H); 7.06 (d, J=5.0 Hz, 1H); 4.25 (d, J=3.4 Hz, 1H); 4.16-4.06 (m, 3H); 4.03 (d, J=4.9 Hz, 2H); 3.75-3.67 (m, 1H); 3.55-3.47 (m, 1H); 3.26 (dd, J=11.3, 9.9 Hz, 1H); 3.03 (d, J=11.9 Hz, 2H); 2.69 (dd, J=13.0, 11.0 Hz, 2H); 2.38 (m, 4H); 2.13-2.03 (m, 3H); 1.95-1.86 (m, 1H).

8-Fluoro-4-[(4-fluoro-4-phenylpiperidin-1-yl)methyl]-N-[(1S,2S)-2-hydroxycyclohexyl]quinoline-2-carboxamide

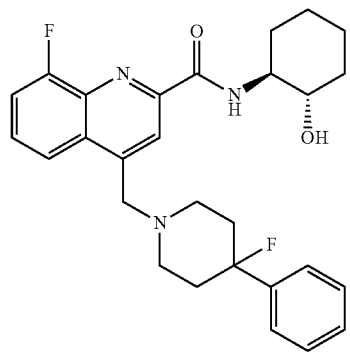

$^1$H NMR (400 MHz, CDCl$_3$): δ 8.43 (s, 1H); 8.23 (d, J=8.1 Hz, 1H); 8.11 (d, J=8.6 Hz, 1H); 7.74 (td, J=8.2, 5.1 Hz, 1H); 7.56 (t, J=8.8 Hz, 1H); 7.40-7.28 (m, 5H); 4.80 (s, 2H); 3.96-3.87 (m, 1H); 3.70-3.59 (m, 3H); 3.38-3.25 (m, 2H); 2.68-2.50 (m, 2H); 2.23-2.08 (m, 4H); 1.81 (d, J=10.4 Hz, 2H); 1.55-1.30 (m, 4H). HRMS 480.2454 M+H⁺.

1,5-Anhydro-2,3-dideoxy-3-[({8-fluoro-4-[(4-fluoro-4-phenylpiperidin-1-yl)methyl]quinolin-2-yl}carbonyl)amino]-L-threo-pentitol

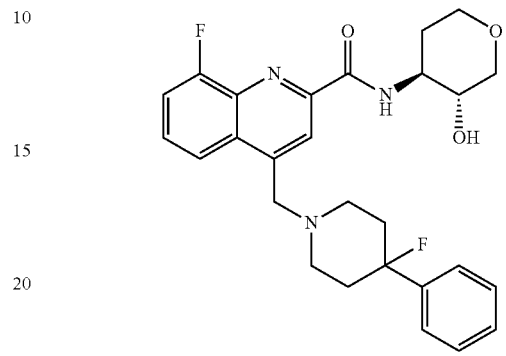

$^1$H NMR (400 MHz, CDCl$_3$): δ 8.45 (s, 1H); 8.28 (d, J=7.3 Hz, 1H); 8.10 (d, J=8.6 Hz, 1H); 7.79-7.72 (m, 1H); 7.60-7.53 (m, 1H); 7.39-7.28 (m, 5H); 4.81 (s, 2H); 4.15-4.00 (m, 3H); 3.78-3.71 (m, 1H); 3.70-3.61 (m, 2H); 3.50 (dd, J=12.6, 10.6 Hz, 1H); 3.37-3.22 (m, 3H); 2.70-2.55 (m, 2H); 2.23-2.05 (m, 3H); 1.93-1.86 (m, 1H). HRMS 482.2249 M+H⁺.

Method B

Representative Example B

4-{[4-Cyano-4-(pyridin-4-yl)piperidin-1-yl]methyl}-N-[(1S,2S)-2-hydroxycyclohexyl]quinoline-2-carboxamide

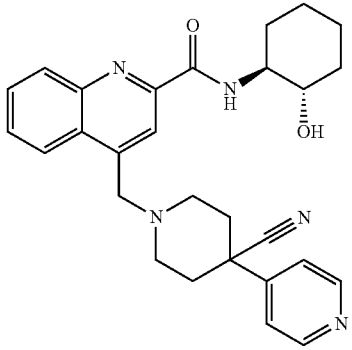 [SMILES: N#CC1(c2ccncc2)CCN(Cc2cc(C(=O)N[C@H]3CCCC[C@@H]3O)nc3ccccc23)CC1]

A solution of ethyl 4-hydroxyquinoline-2-carboxylate (10.0 g, 46.0 mmol) and phosphorus oxybromide (13.2 g, 46.0 mmol) in 100 mL of toluene and 10.0 mL acetonitrile was heated at 75° C. for 1.5 h. The reaction mixture was cooled to room temperature, quenched slowly with water, and extracted with ethyl acetate. The organic fraction was washed with brine, dried over sodium sulfate, filtered, and concentrated. The resultant residue was subjected to silica gel chromatography eluting with 0-50% ethyl acetate in hexanes to afford ethyl 4-bromoquinoline-2-carboxylate that gave a mass ion (ES+) of 280.1 ($^{79}$Br) for M+H⁺.

In a microwave vial containing the above compound (0.50 g, 1.79 mmol), potassium vinyltrifluoroborate (0.36 mg, 2.68 mmol), Pd$_2$(dba)$_3$ (16 mg, 0.018 mmol), and tricyclohexylphosphine (12 mg, 0.043 mmol) was added 5.9 mL of dioxane and 2.4 mL 1.27 M aqueous tribasic potassium phosphate. The reaction was heated to 140° C. in microwave reactor for 30 minutes. The reaction mixture was extracted with methylene chloride, dried over sodium sulfate, filtered, and concentrated. The resultant residue was subjected to silica gel chromatography eluting with 0-40% ethyl acetate in hexanes to afford ethyl 4-ethenylquinoline-2-carboxylate that gave a mass ion (ES+) of 228.2 for M+H$^+$.

A solution of the above compound (0.18 g, 0.77 mmol) in 3.8 mL methylene chloride was cooled to −78° C. Ozone was bubbled into the reaction mixture for 10 min and then 1.2 g polymer-supported triphenylphosphine was added. The reaction mixture was warmed to room temperature, filtered, washed with excess methanol, and concentrated. The resultant residue was subjected to silica gel chromatography eluting with 0-40% ethyl acetate in hexanes to afford ethyl 4-formylquinoline-2-carboxylate that gave a mass ion (ES+) of 230.2 for M+H$^+$.

To a solution of the above compound (0.20 g, 0.86 mmol) in 1.7 mL methanol and 1.7 mL THF was added aqueous 1 N NaOH (0.91 mL, 0.91 mmol). After 3.0 h, the reaction mixture was acidified with 1 N HCl, extracted with ethyl acetate, dried over sodium sulfate, filtered, and concentrated to afford 4-formylquinoline-2-carboxylic acid that gave a mass ion (ES+) of 202.2 for M+H$^+$.

To a solution of the above compound (0.13 g, 0.62 mmol) in 2.5 mL methylene chloride was added (1S,2S)-2-aminocyclohexanol (0.14 g, 1.24 mmol), (benzotriazol-1-yloxy)tris(dimethylamino)phosphonium hexafluorophosphate (BOP) (0.55 g, 1.24 mmol), and triethylamine (0.26 mL, 1.86 mmol). The reaction mixture was stirred at room temperature for 1.5 h, diluted with methylene chloride, washed twice with water, dried over sodium sulfate, filtered, and concentrated. The resultant residue was subjected to silica gel chromatography eluting with 30-100% ethyl acetate in hexanes to afford 4-formyl-N-[(1S,2S)-2-hydroxycyclohexyl]quinoline-2-carboxamide that gave a mass ion (ES+) of 299.3 for M+H$^+$.

To a solution of 4-formyl-N-[(1S,2S)-2-hydroxycyclohexyl]quinoline-2-carboxamide (0.035 g, 0.117 mmol) in 0.50 mL dichloroethane was added 4-cyano-4-(pyridin-4-yl)piperidinium chloride (0.032 g, 0.141 mmol), sodium triacetoxyborohydride (0.037 g, 0.176 mmol), and triethylamine (0.016 mL, 0.117 mmol). The reaction mixture was stirred at room temperature overnight and concentrated. The resultant residue was subjected to purification via reverse phase HPLC. The isolated material was then purified via preparative TLC (7% MeOH/CH$_2$Cl$_2$) to afford the titled compound that gave a mass ion (ES+) of 470.2551 for M+H$^+$.

$^1$H NMR (400 MHz, CDCl$_3$): δ 8.66 (d, J=5.1 Hz, 2H); 8.37 (s, 1H); 8.29 (d, J=7.6 Hz, 1H); 8.24 (d, J=8.5 Hz, 1H); 8.15 (d, J=8.5 Hz, 1H); 7.79 (td, J=7.7, 1.3 Hz, 1H); 7.66 (td, J=7.7, 1.3 Hz, 1H); 7.43 (d, J=5.2 Hz, 2H); 4.11 (s, 2H); 3.94-3.85 (m, 1H); 3.62-3.53 (m, 1H); 3.39 (d, J=4.2 Hz, 1H); 3.07 (dt, J=12.2, 2.7 Hz, 2H); 2.71 (td, J=11.8, 2.7 Hz, 2H); 2.19-2.09 (m, 5H); 1.81 (dt, J=11.9, 2.9 Hz, 2H); 1.53-1.31 (m, 4H).

The following examples were synthesized using Method B

4-{[4-Cyano-4-(pyridin-3-yl)piperidin-1-yl]methyl}-N-[(1S,2S)-2-hydroxycyclohexyl]quinoline-2-carboxamide

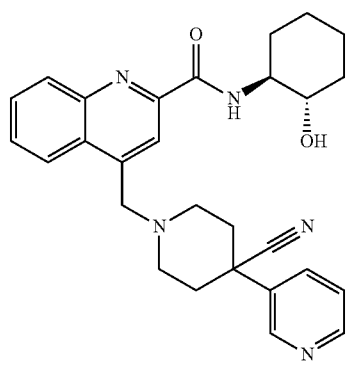 [SMILES: N#CC1(c2cccnc2)CCN(Cc2cc(C(=O)N[C@H]3CCCC[C@@H]3O)nc3ccccc23)CC1]

$^1$H NMR (400 MHz, CDCl$_3$): δ 8.89 (d, J=2.4 Hz, 1H); 8.71 (dd, J=5.0, 1.4 Hz, 1H); 8.40 (s, 1H); 8.29-8.24 (m, 1H); 8.23-8.19 (m, 1H); 8.08-7.99 (m, 1H); 7.88-7.83 (m, 1H); 7.77-7.72 (m, 1H); 7.58 (dd, J=8.2, 5.0 Hz, 1H); 4.51 (s, 2H); 3.95-3.87 (m, 2H); 3.63-3.49 (m, 3H); 3.08 (m, 2H); 2.68-2.10 (m, 5H); 1.82 (d, J=11.3 Hz, 2H); 1.55-1.32 (m, 4H). HRMS: 470.2550 M+H$^+$.

4-[(4-cyano-4-phenylpiperidin-1-yl)methyl]-N-[(1S,2S)-2-hydroxycyclohexyl]quinoline-2-carboxamide

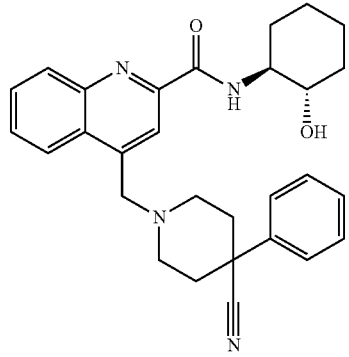 [SMILES: N#CC1(c2ccccc2)CCN(Cc2cc(C(=O)N[C@H]3CCCC[C@@H]3O)nc3ccccc23)CC1]

¹H NMR (400 MHz, CDCl₃): δ 8.42 (s, 1H); 8.26 (d, J=8.2 Hz, 1H); 8.20 (d, J=8.5 Hz, 1H); 7.89 (t, J=7.7 Hz, 1H); 7.79 (t, J=7.6 Hz, 1H); 7.44-7.40 (m, 5H); 4.81 (q, J=11.7 Hz, 2H); 3.93 (m, 1H); 3.83 (m, 2H); 3.64 (m, 1H); 3.34 (q, J=12.5 Hz, 2H); 2.63 (t, J=13.8 Hz, 2H); 2.25 (d, J=14.7 Hz, 2H); 2.19-2.08 (m, 2H); 1.82 (d, J=11.0 Hz, 2H); 1.55-1.30 (m, 4H).

4-{[4-Cyano-4-(2-fluorophenyl)piperidin-1-yl]methyl}-N-[(1S,2S)-2-hydroxycyclohexyl]quinoline-2-carboxamide

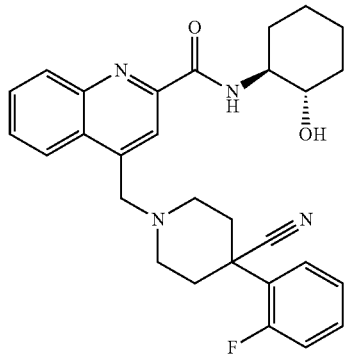

¹H NMR (400 MHz, CDCl₃): δ 8.36 (s, 1H); 8.30-8.23 (m, 2H); 8.14 (d, J=8.5 Hz, 1H); 7.77 (t, J=7.7 Hz, 1H); 7.65 (t, J=7.7 Hz, 1H); 7.45-7.30 (m, 2H); 7.20-7.07 (m, 2H); 4.10 (s, 2H); 3.92-3.83 (m, 1H); 3.62-3.53 (m, 1H); 3.44 (d, J=4.1 Hz, 1H); 3.04 (d, J=11.9 Hz, 2H); 2.75 (td, J=11.2, 3.7 Hz, 2H); 2.33-2.07 (m, 5H); 1.81 (d, J=11.3 Hz, 2H); 1.55-1.31 (m, 4H). HRMS: 487.2511 M+H⁺.

Method C

Representative Example C

4-{[4-(4-Chloropyridin-2-yl)-4-fluoropiperidin-1-yl]methyl}-8-fluoro-N-[(1S,2S)-2-hydroxycyclohexyl]quinoline-2-carboxamide

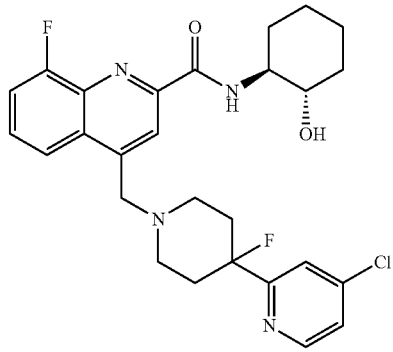 [SMILES: O=C(N[C@H]1CCCC[C@@H]1O)c1cc(CN2CCC(F)(c3cc(Cl)ccn3)CC2)c2cccc(F)c2n1]

To a solution of 2-bromo-4-chloropyridine (C2) (1.00 g, 5.20 mmol) in CH₂Cl₂ (10 mL) cooled to −78° C. was added n-butyllithium (1.6 M in hexanes, 3.57 mL, 5.72 mmol) dropwise. After 15 min, a solution of tert-butyl 4-oxopiperidine-1-carboxylate (C1) (1.14 g, 5.72 mmol) in CH₂Cl₂ (3 mL) was added dropwise. After 1 h, saturated aqueous ammonium chloride (5 mL) was added. The mixture was warmed to ambient temperature, diluted with CH₂Cl₂ and washed with saturated aqueous sodium bicarbonate and brine. The organic solution was dried over sodium sulfate, filtered, and concentrated in vacuo. The resultant residue was purified via silica gel chromatography eluting with 0-20% ethyl acetate in hexanes to provide tert-butyl 4-(4-chloropyridin-2-yl)-4-hydroxypiperidine-1-carboxylate (C3).

To a solution of tert-butyl 4-(4-chloropyridin-2-yl)-4-hydroxypiperidine-1-carboxylate (C3) (0.600 g, 1.92 mmol) in CH₂Cl₂ (10 mL) cooled to −78° C. was added bis(2-methyoxyethyl)aminosulfur trifluoride (Deoxofluor, 0.71 mL, 3.8 mmol). The reaction was slowly warmed to −40° C. over 3 h, then quenched with water (5 mL) and warmed to RT. The mixture was extracted with CH₂Cl₂ (2×) and the combined organic fractions were washed with brine, dried over sodium sulfate, filtered, and concentrated in vacuo. The resultant residue was purified via silica gel chromatography eluting with 10-40% ethyl acetate in hexanes to provide tert-butyl 4-(4-chloropyridin-2-yl)-4-fluoropiperidine-1-carboxylate (C4).

A solution of tert-butyl 4-(4-chloropyridin-2-yl)-4-fluoropiperidine-1-carboxylate (C4) (0.280 g, 0.890 mmol) in ethyl acetate (10 mL) was saturated with HCl₍g₎. After 1 h, the reaction was concentrated in vacuo to provide 4-chloro-2-(4-fluoropiperidin-4-yl)pyridine dihydrochloride (C5) that gave a mass ion (ES+) of 215.2 for M+H⁺.

To a solution of 4-bromo-8-fluoroquinoline-2-carboxylic acid (C6) (1.34 g, 4.96 mmol) in dichloromethane (20 mL) was added (1S,2S)-2-aminocyclohexanol (0.857 g, 7.44 mmol), benzotriazol-1-yl-oxy-tris(dimethylamino)phosphonium hexafluorophosphate (2.63 g, 5.95 mmol), and triethylamine (1.04 mL, 7.44 mmol). After 17 h, the mixture was diluted with dichloromethane and washed with saturated aqueous sodium bicarbonate (1×) and brine (1×), dried over sodium sulfate, filtered, and concentrated in vacuo. The resultant residue was purified via silica gel chromatography eluting with 0-3% methanol in dichloromethane to provide 4-bromo-8-fluoro-N-[(1S,2S)-2-hydroxycyclohexyl]quinoline-2-carboxamide (C7) that gave a mass ion (ES+) of 368.8 (⁸¹Br) for M+H⁺.

To a solution of 4-bromo-8-fluoro-N-[(1S,2S)-2-hydroxycyclohexyl]quinoline-2-carboxamide (C7) (1.88 g, 5.12 mmol) in 10:1 THF:H₂O (22 mL) was added potassium vinyltrifluoroborate (2.06 g, 15.4 mmol) and cesium carbonate (3.34 g, 10.2 mmol). The reaction was placed under N₂₍g₎, and [1,1'-bis(diphenylphosphino)-ferrocene]dichloro palladium (II), complex with dichloromethane (0.100 g, 0.122 mmol) was added. The mixture was heated to 100° C. for 3 h, then cooled to RT and diluted with ethyl acetate. The organic solution was washed with saturated aqueous sodium bicarbonate (1×) and brine (1×), dried over sodium sulfate, filtered, and concentrated in vacuo. The resultant residue was purified via silica gel chromatography eluting with 0-5% methanol in dichloromethane to provide 4-ethenyl-8-fluoro-N-[(1S,2S)-2-hydroxycyclohexyl]quinoline-2-carboxamide (C8) that gave a mass ion (ES+) of 315.1 for M+H$^+$.

To a solution of 4-ethenyl-8-fluoro-N-[(1S,2S)-2-hydroxycyclohexyl]quinoline-2-carboxamide (1.10 g, 3.50 mmol) in 2:1 THF:H$_2$O (21 mL) was added 4-methylmorpholine N-oxide (0.820 g, 7.00 mmol) and osmium tetroxide (0.055 mL, 0.18 mmol). After 3 h, additional 4-methylmorpholine N-oxide (0.205 g, 1.75 mmol) and osmium tetroxide (0.055 mL, 0.18 mmol) were added. After 18 h, the mixture was diluted with ethyl acetate, and filtered to remove a pale orange solid. The organic filtrate was washed with saturated aqueous sodium bisulfite (2×) and brine (1×), dried over sodium sulfate, filtered, and concentrated in vacuo to provide the diol intermediate that gave a mass ion (ES+) of 349.1 for M+H$^+$.

To a solution of the diol (1.20 g, 3.44 mmol) in 2:1 THF:H$_2$O (21 mL) was added sodium periodate (0.810 g, 3.79 mmol). After 1 h, the mixture was diluted with ethyl acetate, washed with water (1×) and brine (1×), dried over sodium sulfate, filtered, and concentrated in vacuo. The resultant residue was purified via silica gel chromatography eluting with 0-50% ethyl acetate in hexanes to provide 8-fluoro-4-formyl-N-[(1S,2S)-2-hydroxycyclohexyl]quinoline-2-carboxamide (C9) that gave a mass ion (ES+) of 317.1 for M+H$^+$.

To a solution of 8-fluoro-4-formyl-N-[(1S,2S)-2-hydroxycyclohexyl]quinoline-2-carboxamide (C9) (0.080 g, 0.25 mmol) in DCE (3 mL) was 4-chloro-2-(4-fluoropiperidin-4-yl)pyridine dihydrochloride (C5) (0.080 g, 0.28 mmol) and triethylamine (6 drops). After 5 min, acetic acid (0.043 mL, 0.76 mmol) and MP-cyanoborohydride were added. The mixture was irradiated in a microwave reactor at 100° C. for 20 min, then diluted with CH$_2$Cl$_2$ and was washed with brine. The organic solution was dried over sodium sulfate, filtered, and concentrated in vacuo. The resultant residue was purified via silica gel chromatography eluting with 0-5% methanol in dichloromethane to provide the title compound (Example C) as a white solid that gave a proton NMR spectra consistent with theory and a mass ion (ES+) of 515.0 for M+H$^+$. $^1$H NMR (400 MHz, CDCl$_3$) δ 8.44 (d, J=5.2 Hz, 1H), 8.38 (s, 1H), 8.29 (d, J=7.8 Hz, 1H), 8.17 (d, J=8.5 Hz, 1H), 7.60-7.55 (m, 2H), 7.47-7.42 (m, 1H), 7.22-7.20 (m, 1H), 4.03 (s, 2H), 3.94-3.86 (m, 1H), 3.63-3.56 (m, 1H), 3.42 (br s, 1H), 2.86-2.83 (m, 2H), 2.62-2.56 (m, 2H), 2.47-2.30 (m, 2H), 2.17-2.11 (m, 2H), 1.89-1.78 (m, 4H), 1.56-1.31 (m, 4H).

Method D

Example D

8-Fluoro-4-{[4-fluoro-4-(4-methylpyridin-2-yl)piperidin-1-yl]methyl}-N-[(1S,2S)-2-hydroxycyclohexyl]quinoline-2-carboxamide

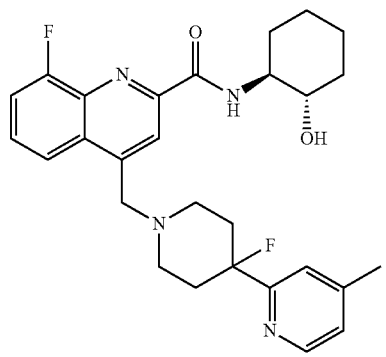 [SMILES: Cc1ccnc(C2(F)CCN(Cc3cc(C(=O)N[C@H]4CCCC[C@@H]4O)nc4c(F)cccc34)CC2)c1]

To a solution of 4-{[4-(4-chloropyridin-2-yl)-4-fluoropiperidin-1-yl]methyl}-8-fluoro-N-[(1S,2S)-2-hydroxycyclohexyl]quinoline-2-carboxamide (Example C) (0.022 g, 0.043 mmol) in THF (3 mL) under an atmosphere of nitrogen was added dimethyl zinc (2.0 M in THF, 0.043 mL, 0.085 mmol) and tetrakis(triphenylphosphine)palladium(0) (0.0011 mg, 0.00090 mmol). The reaction was heated to 90° C., cooled to RT, and retreated with additional dimethyl zinc (2.0 M in THF, 0.043 mL, 0.085 mmol) and tetrakis(triphenylphosphine)palladium(0) (0.0011 mg, 0.00090 mmol). The reaction was heated to 100° C. for 5 h, then at 50° C. for an additional 16 h. The mixture was cooled to RT, diluted with ethyl acetate, and washed with saturated aqueous sodium bicarbonate and brine. The organic solution was dried over sodium sulfate, filtered, and concentrated in vacuo. The resultant residue was purified via silica gel chromatography eluting with 0-5% MeOH in dichloromethane to provide the title compound (Example D) as a white solid that gave a proton NMR spectra consistent with theory and a mass ion (ES+) of 495.1 for M+H$^+$. $^1$H NMR (400 MHz, CDCl$_3$) δ 8.39-8.36 (m, 2H), 8.30-8.20 (m, 2H), 7.69-7.38 (m, 3H), 7.00 (br s, 1H), 4.03 (s, 2H), 3.89 (br s, 1H), 3.59-3.49 (m, 1H), 3.48-3.14 (m, 1H), 2.85-2.81 (m, 2H), 2.61-2.57 (m, 2H), 2.44-2.37 (m, 2H), 2.37 (s, 3H), 2.18-2.13 (m, 2H), 1.87-1.79 (m, 4H), 1.50-1.14 (m, 4H).

The following compounds in Table 1 were prepared according to referenced procedure, and in the Examples above. The starting materials are either commercially available or known in the literature, or may be prepared from commercially available reagents using convetional reactions well known in the art.

TABLE 1

| Example | Structure | Name | M + 1 | Method |
|---|---|---|---|---|
| 1 | 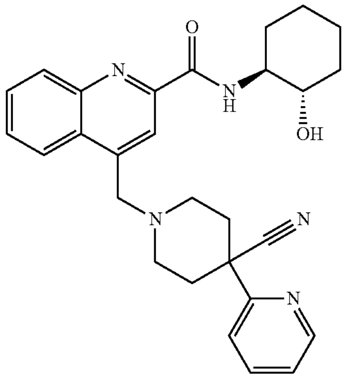 [SMILES: N#CC1(c2ccccn2)CCN(Cc2cc(C(=O)N[C@H]3CCCC[C@@H]3O)nc3ccccc23)CC1] | 4-[(4-cyano-4-pyridin-2-ylpiperidin-1-yl)methyl]-N-[(1S,2S)-2-hydroxycyclohexyl]quinoline-2-carboxamide | 470.3 | A |
| 2 | 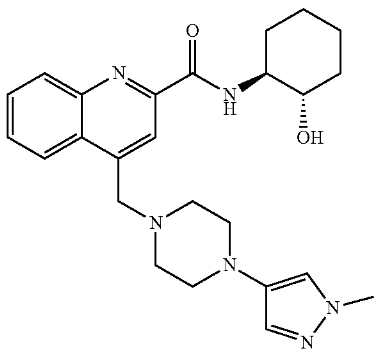 [SMILES: Cn1cc(N2CCN(Cc3cc(C(=O)N[C@H]4CCCC[C@@H]4O)nc4ccccc34)CC2)cn1] | N-[(1S,2S)-2-hydroxycyclohexyl]-4-{[4-(1-methyl-1H-pyrazol-4-yl)piperazin-1-yl]methyl}quinoline-2-carboxamide | 449.3 | A |
| 3 | 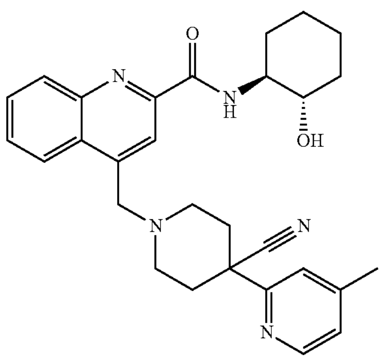 [SMILES: Cc1ccnc(C2(C#N)CCN(Cc3cc(C(=O)N[C@H]4CCCC[C@@H]4O)nc4ccccc34)CC2)c1] | 4-{[4-cyano-4-(4-methylpyridin-2-yl)piperidin-1-yl]methyl}-N-[(1S,2S)-2-hydroxycyclohexyl]quinoline-2-carboxamide | 484.3 | A |
| 4 | 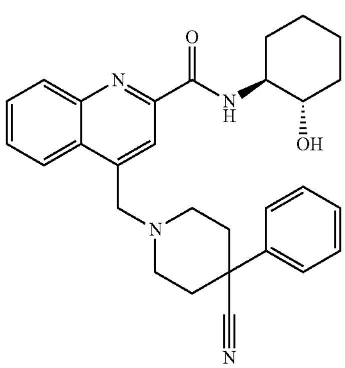 [SMILES: N#CC1(c2ccccc2)CCN(Cc2cc(C(=O)N[C@H]3CCCC[C@@H]3O)nc3ccccc23)CC1] | 4-[(4-cyano-4-phenylpiperidin-1-yl)methyl]-N-[(1S,2S)-2-hydroxycyclohexyl]quinoline-2-carboxamide | 469.3 | B |

TABLE 1-continued

| Example | Structure | Name | M + 1 | Method |
|---|---|---|---|---|
| 5 | 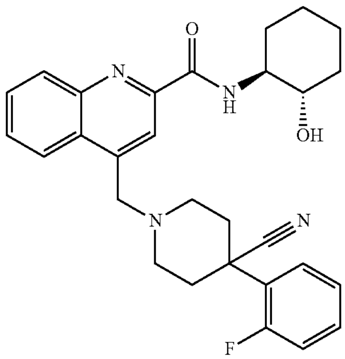 [SMILES: N#CC1(c2ccccc2F)CCN(Cc2cc(C(=O)N[C@H]3CCCC[C@@H]3O)nc3ccccc23)CC1] | 4-{[4-cyano-4-(2-fluorophenyl)piperidin-1-yl]methyl}-N-[(1S,2S)-2-hydroxycyclohexyl]quinoline-2-carboxamide | 487.3 | B |
| 6 | 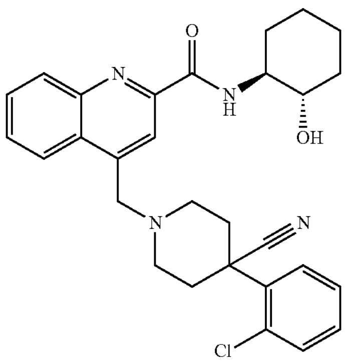 | 4-{[4-(2-chlorophenyl)-4-cyanopiperidin-1-yl]methyl}-N-[(1S,2S)-2-hydroxycyclohexyl]quinoline-2-carboxamide | 503.2 | A |
| 7 | 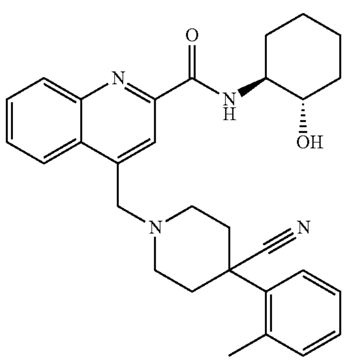 [SMILES: Cc1ccccc1C1(C#N)CCN(Cc2cc(C(=O)N[C@H]3CCCC[C@@H]3O)nc3ccccc23)CC1] | 4-{[4-cyano-4-(2-methylphenyl)piperidin-1-yl]methyl}-N-[(1S,2S)-2-hydroxycyclohexyl]quinoline-2-carboxamide | 483.3 | A |
| 8 | 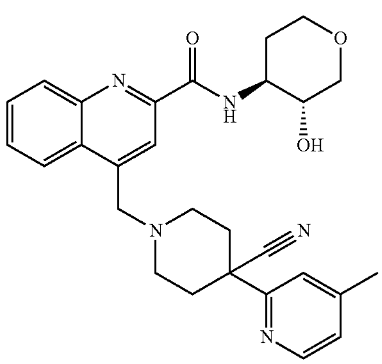 [SMILES: Cc1ccnc(C2(C#N)CCN(Cc3cc(C(=O)N[C@H]4CCOC[C@@H]4O)nc4ccccc34)CC2)c1] | 1,5-anhydro-3-{[(4-{[4-cyano-4-(4-methylpyridin-2-yl)piperidin-1-yl]methyl}quinolin-2-yl)carbonyl]amino}-2,3-dideoxy-L-threo-pentitol | 486.3 | A |

TABLE 1-continued

| Example | Structure | Name | M + 1 | Method |
|---|---|---|---|---|
| 9 | 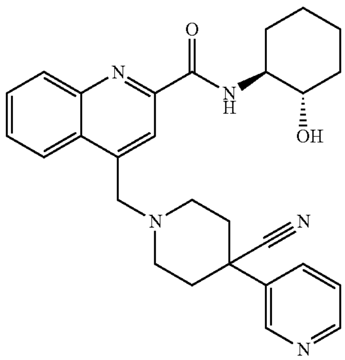 [SMILES: N#CC1(c2cccnc2)CCN(Cc2cc(C(=O)N[C@H]3CCCC[C@@H]3O)nc3ccccc23)CC1] | 4-[(4-cyano-4-pyridin-3-ylpiperidin-1-yl)methyl]-N-[(1S,2S)-2-hydroxycyclohexyl]quinoline-2-carboxamide | 470.3 | B |
| 10 | 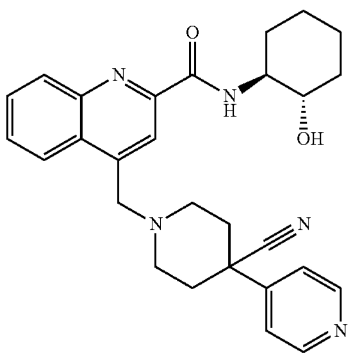 [SMILES: N#CC1(c2ccncc2)CCN(Cc2cc(C(=O)N[C@H]3CCCC[C@@H]3O)nc3ccccc23)CC1] | 4-[(4-cyano-4-pyridin-4-ylpiperidin-1-yl)methyl]-N-[(1S,2S)-2-hydroxycyclohexyl]quinoline-2-carboxamide | 470.3 | B |
| 11 | 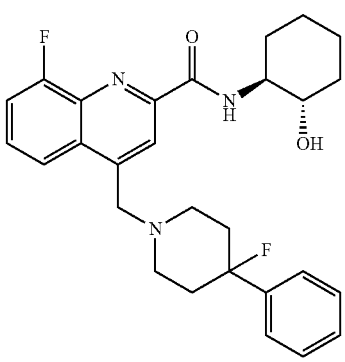 [SMILES: O=C(N[C@H]1CCCC[C@@H]1O)c1cc(CN2CCC(F)(c3ccccc3)CC2)c2cccc(F)c2n1] | 8-fluoro-4-[(4-fluoro-4-phenylpiperidin-1-yl)methyl]-N-[(1S,2S)-2-hydroxycyclohexyl]quinoline-2-carboxamide | 480.2 | C |
| 12 | 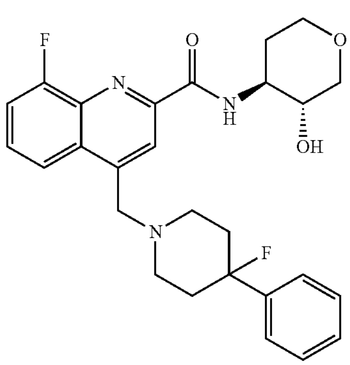 [SMILES: O=C(N[C@H]1CCOC[C@@H]1O)c1cc(CN2CCC(F)(c3ccccc3)CC2)c2cccc(F)c2n1] | 1,5-anhydro-2,3-dideoxy-3-[({8-fluoro-4-[(4-fluoro-4-phenylpiperidin-1-yl)methyl]quinolin-2-yl}carbonyl)amino]-L-threo-pentitol | 482.2 | C |

TABLE 1-continued

| Example | Structure | Name | M + 1 | Method |
|---|---|---|---|---|
| 13 | 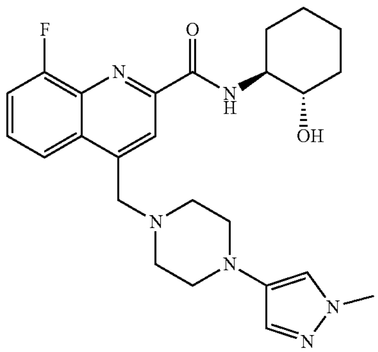 [SMILES: Cn1cc(N2CCN(Cc3cc(C(=O)N[C@H]4CCCC[C@@H]4O)nc4c(F)cccc34)CC2)cn1] | 8-fluoro-N-[(1S,2S)-2-hydroxycyclohexyl]-4-{[4-(1-methyl-1H-pyrazol-4-yl)piperazin-1-yl]methyl}quinoline-2-carboxamide | 467.1 | C |
| 14 | 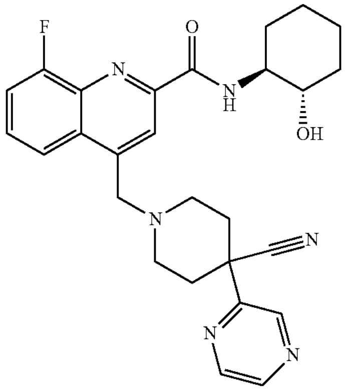 [SMILES: N#CC1(c2cnccn2)CCN(Cc2cc(C(=O)N[C@H]3CCCC[C@@H]3O)nc3c(F)cccc23)CC1] | 4-[(4-cyano-4-pyrazin-2-ylpiperidin-1-yl)methyl]-8-fluoro-N-[(1S,2S)-2-hydroxycyclohexyl]quinoline-2-carboxamide | 489.1 | C |
| 15 | 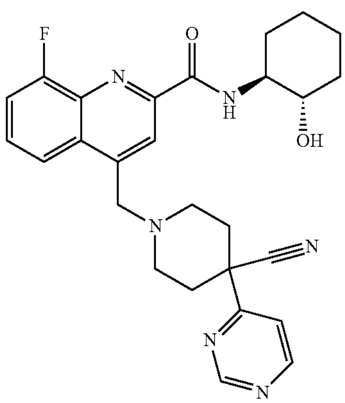 [SMILES: N#CC1(c2ccncn2)CCN(Cc2cc(C(=O)N[C@H]3CCCC[C@@H]3O)nc3c(F)cccc23)CC1] | 4-[(4-cyano-4-pyrimidin-4-ylpiperidin-1-yl)methyl]-8-fluoro-N-[(1S,2S)-2-hydroxycyclohexyl]quinoline-2-carboxamide | 489.1 | C |
| 16 | 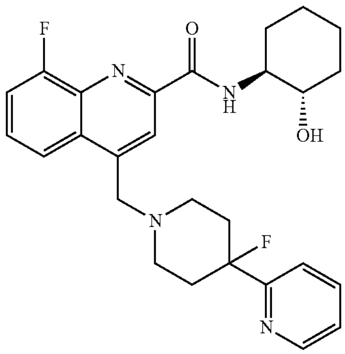 | 8-fluoro-4-[(4-fluoro-4-pyridin-2-ylpiperidin-1-yl)methyl]-N-[(1S,2S)-2-hydroxycyclohexyl]quinoline-2-carboxamide | 481.1 | C |

TABLE 1-continued

| Example | Structure | Name | M + 1 | Method |
|---|---|---|---|---|
| 17 | 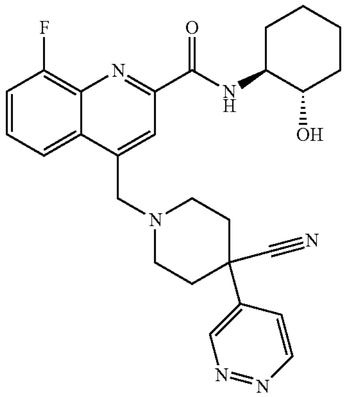 [SMILES: N#CC1(c2ccnnc2)CCN(Cc2cc(C(=O)N[C@H]3CCCC[C@@H]3O)nc3c(F)cccc23)CC1] | 4-[(4-cyano-4-pyridazin-4-ylpiperidin-1-yl)methyl]-8-fluoro-N-[(1S,2S)-2-hydroxycyclohexyl]quinoline-2-carboxamide | 489.0 | C |
| 18 | 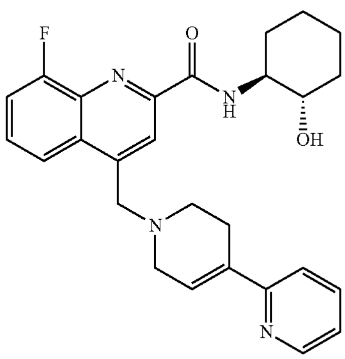 [SMILES: O=C(N[C@H]1CCCC[C@@H]1O)c1cc(CN2CC=C(c3ccccn3)CC2)c2cccc(F)c2n1] | 4-(3',6'-dihydro-2,4'-bipyridin-1'(2'H)-ylmethyl)-8-fluoro-N-[(1S,2S)-2-hydroxycyclohexyl]quinoline-2-carboxamide | 461.0 | C |
| 19 | 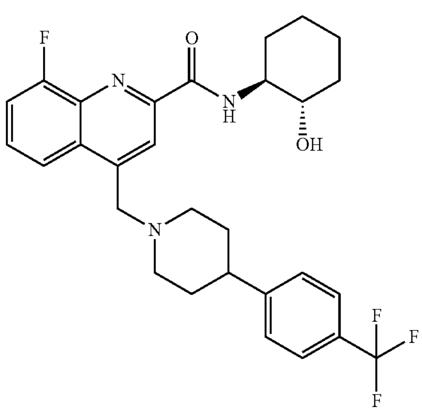 [SMILES: O=C(N[C@H]1CCCC[C@@H]1O)c1cc(CN2CCC(c3ccc(C(F)(F)F)cc3)CC2)c2cccc(F)c2n1] | 8-fluoro-N-[(1S,2S)-2-hydroxycyclohexyl]-4-({4-[4-(trifluoromethyl)phenyl]piperidin-1-yl}methyl)quinoline-2-carboxamide | 530.1 | C |
| 20 | 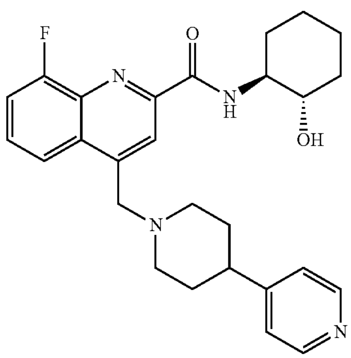 [SMILES: O=C(N[C@H]1CCCC[C@@H]1O)c1cc(CN2CCC(c3ccncc3)CC2)c2cccc(F)c2n1] | 8-fluoro-N-[(1S,2S)-2-hydroxycyclohexyl]-4-[(4-pyridin-4-ylpiperidin-1-yl)methyl]quinoline-2-carboxamide | 463.0 | C |

TABLE 1-continued

| Example | Structure | Name | M + 1 | Method |
|---|---|---|---|---|
| 21 | 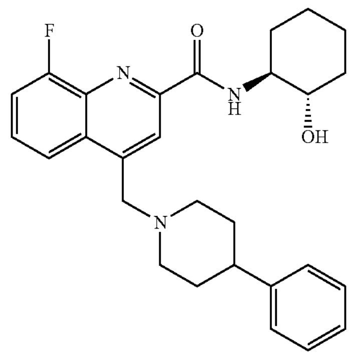 [SMILES: O=C(N[C@H]1CCCC[C@@H]1O)c1cc(CN2CCC(c3ccccc3)CC2)c2cccc(F)c2n1] | 8-fluoro-N-[(1S,2S)-2-hydroxycyclohexyl]-4-[(4-phenylpiperidin-1-yl)methyl]quinoline-2-carboxamide | 462.0 | C |
| 22 | 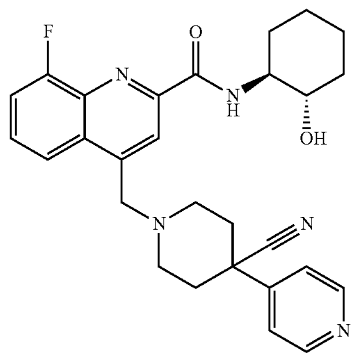 [SMILES: N#CC1(c2ccncc2)CCN(Cc2cc(C(=O)N[C@H]3CCCC[C@@H]3O)nc3c(F)cccc23)CC1] | 4-[(4-cyano-4-pyridin-4-ylpiperidin-1-yl)methyl]-8-fluoro-N-[(1S,2S)-2-hydroxycyclohexyl]quinoline-2-carboxamide | 488.1 | C |
| 23 | 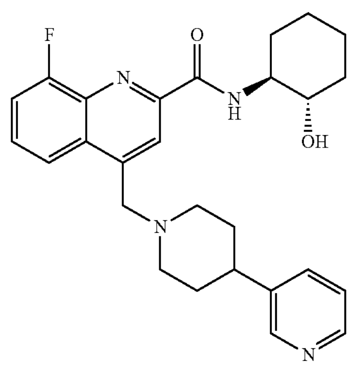 [SMILES: O=C(N[C@H]1CCCC[C@@H]1O)c1cc(CN2CCC(c3cccnc3)CC2)c2cccc(F)c2n1] | 8-fluoro-N-[(1S,2S)-2-hydroxycyclohexyl]-4-[(4-pyridin-3-ylpiperidin-1-yl)methyl]quinoline-2-carboxamide | 463.1 | C |
| 24 | 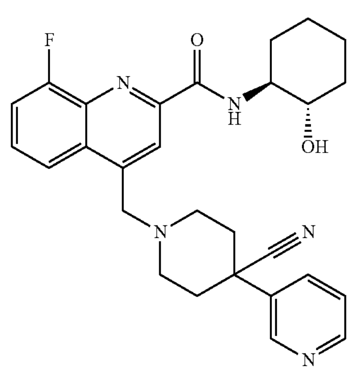 [SMILES: N#CC1(c2cccnc2)CCN(Cc2cc(C(=O)N[C@H]3CCCC[C@@H]3O)nc3c(F)cccc23)CC1] | 4-[(4-cyano-4-pyridin-3-ylpiperidin-1-yl)methyl]-8-fluoro-N-[(1S,2S)-2-hydroxycyclohexyl]quinoline-2-carboxamide | 488.1 | C |

TABLE 1-continued

| Example | Structure | Name | M + 1 | Method |
|---|---|---|---|---|
| 25 | 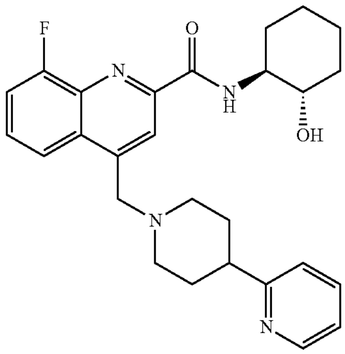 [SMILES: O=C(N[C@H]1CCCC[C@@H]1O)c1cc(CN2CCC(c3ccccn3)CC2)c2cccc(F)c2n1] | 8-fluoro-N-[(1S,2S)-2-hydroxycyclohexyl]-4-[(4-pyridin-2-ylpiperidin-1-yl)methyl]quinoline-2-carboxamide | 463.1 | C |
| 26 | 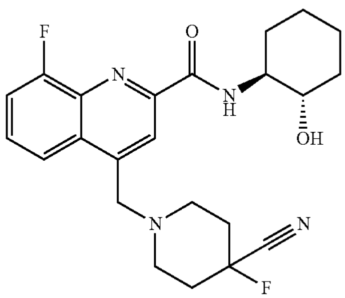 [SMILES: N#CC1(F)CCN(Cc2cc(C(=O)N[C@H]3CCCC[C@@H]3O)nc3c(F)cccc23)CC1] | 4-[(4-cyano-4-fluoropiperidin-1-yl)methyl]-8-fluoro-N-[(1S,2S)-2-hydroxycyclohexyl]quinoline-2-carboxamide | 429.1 | C |
| 27 | 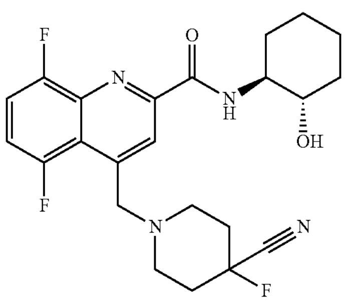 [SMILES: N#CC1(F)CCN(Cc2cc(C(=O)N[C@H]3CCCC[C@@H]3O)nc3c(F)ccc(F)c23)CC1] | 4-[(4-cyano-4-fluoropiperidin-1-yl)methyl]-5,8-difluoro-N-[(1S,2S)-2-hydroxycyclohexyl]quinoline-2-carboxamide | 447.1 | C |
| 28 | 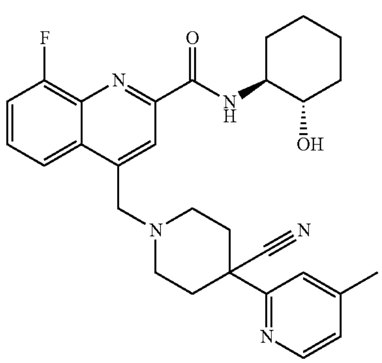 [SMILES: Cc1ccnc(C2(C#N)CCN(Cc3cc(C(=O)N[C@H]4CCCC[C@@H]4O)nc4c(F)cccc34)CC2)c1] | 4-{[4-cyano-4-(4-methylpyridin-2-yl)piperidin-1-yl]methyl}-8-fluoro-N-[(1S,2S)-2-hydroxycyclohexyl]quinoline-2-carboxamide | 502.1 | C |

TABLE 1-continued

| Example | Structure | Name | M + 1 | Method |
|---|---|---|---|---|
| 29 | 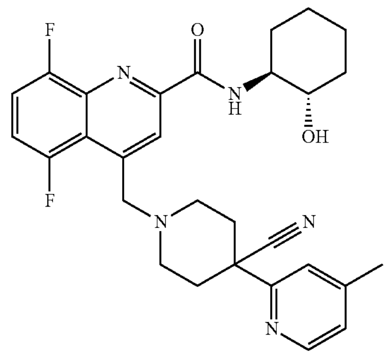 [SMILES: Cc1ccnc(C2(C#N)CCN(Cc3cc(C(=O)N[C@H]4CCCC[C@@H]4O)nc4c(F)ccc(F)c34)CC2)c1] | 4-{[4-cyano-4-(4-methylpyridin-2-yl)piperidin-1-yl]methyl}-5,8-difluoro-N-[(1S,2S)-2-hydroxycyclohexyl]quinoline-2-carboxamide | 520.1 | C |
| 30 | 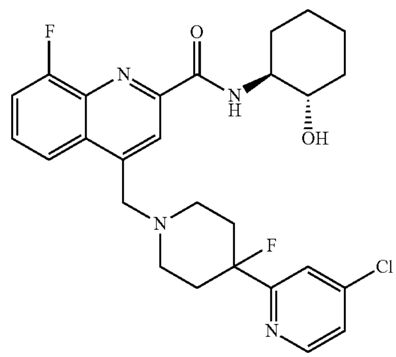 [SMILES: O=C(N[C@H]1CCCC[C@@H]1O)c1cc(CN2CCC(F)(c3cc(Cl)ccn3)CC2)c2cccc(F)c2n1] | 4-{[4-(4-chloropyridin-2-yl)-4-fluoropiperidin-1-yl]methyl}-8-fluoro-N-[(1S,2S)-2-hydroxycyclohexyl]quinoline-2-carboxamide | 515.1 | C |
| 31 | 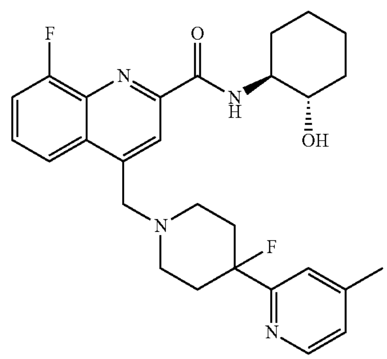 [SMILES: Cc1ccnc(C2(F)CCN(Cc3cc(C(=O)N[C@H]4CCCC[C@@H]4O)nc4c(F)cccc34)CC2)c1] | 8-fluoro-4-{[4-fluoro-4-(4-methylpyridin-2-yl)piperidin-1-yl]methyl}-N-[(1S,2S)-2-hydroxycyclohexyl]quinoline-2-carboxamide | 495.1 | D |

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a FLIPR$^{384}$ Fluorometric Imaging Plate Reader System. The assay studies the effect of one or several concentrations of test compounds on basal or acetylcholine-stimulated $Ca^{2+}$ levels using FLIPR.

Compounds are prepared and subjected to a preincubation period of 4 min. Thereafter, a single $EC_{20}$ concentration of acetylcholine is added to each well (3 nM final). The intracellular $Ca^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 μL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 120 μL addition plate; 96-well Whatman 2 ml Uniplate Incubator, 37° C., 5% $CO_2$; Skatron EMBLA-384 Plate Washer; Multimek Pipetting System; Genesis Freedom 200 System; Mosquito System; Temo Nanoliter Pipetting System; and FLIPR384 Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 μM in buffer for a final concentration of 1 μM in Assay. 20% Pluronic Acid Solution stock, with concentration of 0.04% in Buffer, 0.02% in Assay.

65 μl, of 2 mM Fluo-4AM are mixed with 130 μL of 20% Pluronic Acid. The resulting solution and 650 μL FBS is added to the assay buffer for a total volume of 65 mL. Positive Controls: 4-Br-A23187: 10 mM in DMSO; final concentration 10 μM. Acetylcholine: 10 mM in water, working stock at both 20 μM and 30 μM in assay buffer, final concentration of 10 μM. This is used to check the maximum stimulation of the CHOK1/hM1 cells. 20 μM (2×) acetylcholine is added in the preincubation part of the assay, and the 30 μM (3×) stock is added in the second part. ($EC_{20}$)Acetylcholine: 10 mM in water, working stock of 9 nM (3×), and final concentration in assay is 3 nM. This is used after the preincubation with test compounds. Addition of the $EC_{20}$ Acetylcholine to each well with a test compound will ascertain any modulator activity. 24 wells contain 3 nM Acetylcholine alone as a control.

Determining Activity of Putative Compounds:

Screening Plate: Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanoliter Pipetting System by transferring 1 μl of serial diluted compounds to each well, and 1 mM acetylcholine (100× stock concentration) were added as a control. Using Temo, 49 μl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 μM acetylcholine control (3×) is added into control wells, and the 3× agonist plate is transferred into a 384 well plate.

Cells are washed three times with 100 μL of buffer, leaving 30 μL of buffer in each well. Using Multimek, 30 μL, of Dye Loading Buffer is added into each well and incubated at 37° C., 5% $CO_2$ for up to one hr.

After 60 mM, the cells are washed three times with 100 μL of buffer, leaving 30 μL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the $EC_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 μM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 2 below:

| Example | IP Value (nM) |
|---|---|
| 1 | 54 |
| 2 | 369 |
| 3 | 20 |
| 4 | 325 |
| 5 | 81 |
| 6 | 117 |
| 7 | 136 |
| 8 | 27 |

-continued

| Example | IP Value (nM) |
|---|---|
| 9 | 54 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (I):

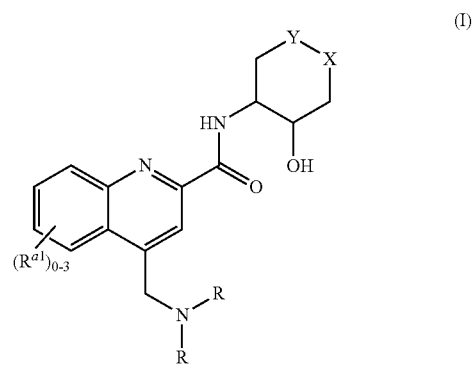

and pharmaceutically acceptable salts thereof, wherein
X=Y=$CH_2$, X=O and Y=$CH_2$, or X=$CH_2$ and Y=O;
each R is selected from the group consisting of
(1) hydrogen,
(2) $C_{6-10}$aryl,
(3) $C_{5-10}$ heterocycle, optionally substituted with 1 to 3 groups of $R^a$,
(4) —$C_{1-6}$ alkyl, optionally substituted with 1 to 3 groups of $R^a$,
(5) —$C_{2-6}$ alkenyl, optionally substituted with 1 to 3 groups of $R^a$,
(6) —S(=O)$_n$—$R^1$,
(7) —OH,
(8) or R and R can be linked together with the nitrogen to which they are both attached to form a 3-6membered saturated heterocyclic ring, wherein one or two of the ring carbon atoms are optionally replaced by a nitrogen, oxygen or sulfur; wherein said saturated 25 heterocyclic ring is optionally susbstituted with 1 to 3 groups of $R^a$,
$R^a$ and $R^{a1}$ are independently selected from the group consisting of:
(1) hydroxyl,
(2) halogen,
(3) $C_{1-6}$alkyl,
(4) $C_{6-10}$aryl, which is unsubstituted or substituted with 1 to 3 groups of $R^b$,
(5) ($CH_2$)$_n$heterocyclyl, which is unsubstituted or substituted with 1 to 3 groups of $R^b$, and
(6) —CN,
$R^b$ is selected from the group consisting of:
(1) hydroxyl,
(2) halogen, (3) C$_{1-6}$alkyl, and
(4) C$_{1-4}$haloalkyl,
R$^1$ is selected from the group consisting of:
(1) hydrogen,
(2) —C$_{1-6}$ alkyl,
(3) —C$_{2-6}$ alkenyl, and
(4) —N(R$^1$)$_2$
n is 0-4.

2. The compound according to claim 1 of formula (I) wherein X═O and Y═CH$_2$.

3. The compound according to claim 1 of formula (I) wherein X═Y═CH$_2$.

4. The compound according to claim 1 of formula (I) wherein R and R are linked together with the nitrogen to which they are both attached to form a 3-6 membered saturated heterocyclic ring, wherein one or two of the ring carbon atoms is optionally replaced by a nitrogen, oxygen or sulfur; and wherein said saturated heterocyclic ring is optionally susbstituted with 1 to 3 groups of R$^a$.

5. The compound according to claim 4 of formula (I) wherein the heterocyclic ring formed by linking R and R is optionally substituted piperidinyl or piperazinyl.

6. The compound according to claim 1 of formula (I) whereinR$^a$ is selected from the group consisting of halogen, CN, and optionally substituted phenyl, pyridyl, pyrazolyl, pyrazinyl, pyrimidinyl and pyradazinyl.

7. The compound according to claim 1 of formula (I) represented by structural formula Ia:

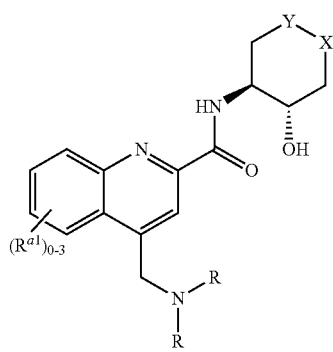

Ia or a pharmceutically acceptable salt thereof.

8. The compound according to claim 7 represented by structural formula Ib:

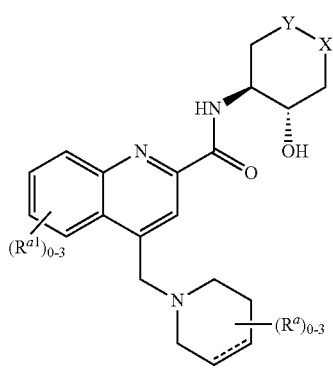

Ib or a pharmaceutically acceptable salt thereof wherein X, Y and R$^a$ are as originally described and—represents a bond that is present or absent.

9. The compound according to claim 8 wherein X═Y═CH$_2$ or X═O and Y═CH$_2$, —is absent, and R$^a$ is selected from the group consisting of CN, halo, and optionally substituted phenyl, pyridyl, pyrazolyl, pyrazinyl, pyrimidinyl and pyradazinyl.

10. The compound according to claim 7 represented by the structural formula Ic:

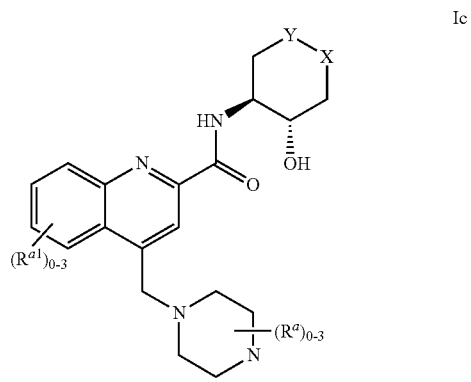

Ic or a pharmaceutically acceptable salt thereof.

11. The compound according to claim 10 wherein X═Y═CH$_2$ or X═O and Y═CH$_2$, and R$^a$ is selected from the group consisting of CN, halo, and optionally substituted phenyl, pyridyl, pyrazolyl, pyrazinyl, pyrimidinyl and pyradazinyl.

12. A compound which is
4-[(4-cyano-4-pyridin-2-ylpiperidin-1-yl)methyl]-N-[(1S,2S)-2-hydroxycyclohexyl]quinoline-2-carboxamide,
N-[(1S,2S)-2-hydroxycyclohexyl]-4-{[4-(1-methyl-1H-pyrazole-4-yl)piperzin-1-yl]methyl}quinoline-2-,
4-{[4-cyano-4-(4-methylpyridin-2-yl)piperidin-1-yl]methyl}-N-[(1S,2S)-2-hydroxycyclohexyl]quinoline-2-carboxamide,
4-[(4-cyano-4-phenylpiperidin-1-yl)methyl]-N-[(1S,2S)-2-hydroxycyclohexyl]quinoline-2-carbozamide,
4-{[4-cyano-4-(2-fluorophenyl)piperidin-1-yl]methyl}-N-[(1S,2S)-2-hydroxycyclohexyl]quinoline-2-carboxamide,
4-{[4-(2-chlorophenyl)-4-cyanopiperidin-1-yl]methyl}-N-[(1S,2S)-2-hydroxycyclohexyl]quinoline-2-carboxamide,
4-{[4-cyano-4-(2-methylphenyl)piperidin-1-yl]methyl}-N-[(1S,2S)-2-hydroxycyclohexyl]quinoline-2-carboxamide,
1,5-anhydro-3-{[(4-{[4-cyano-4-(4-methylpyridin-2-yl)piperidin-1-yl]methyl}quinoline-2-yl)carbonyl]amino}-2,3-dideoxy-L-threo-penitol,
4-[(4-cyano-4-pyridin-3-ylpiperidin-1-yl)methyl]-N-[(1S,2S)-2-hydroxycyclohexyl]quinoline-2-carboxamide,
4-[(4-cyano-4-pyridin-4-ylpiperidin-1-yl)methyl]-N-[(1S,2S)-2-hydroxycyclohexyl]quinoline-2-carboxamide,
8-fluoro-4-[(4-fluoro-[(4-phenylpiperidin-1-yl)methyl]-N-(1S,2S)-2-hydroxycyclohexyl]quinoline-2-carboxamide,
1,5-anhydro-2,3-dideoxy-3-[({8-fluoro-4-[(4-fluoro-4-phenylpiperidin-1-yl)methyl]quinoline-2-yl}carbonyl)amino]-L-threo-penitol,
8-fluro-N-[(1S,2S)-2-hydroxycyclohexyl]-4-{[4-(1-methyl-1H-pyrazol-4-yl)piperazin-1-yl]methyl}quinoline-2-carboxamide,
4-[(4-cyano-4-pyrazin-2-ylpiperidin-1-yl)methyl]8-fluoro-N-[(1S,2S)-2-hydroxycyclohexyl]quinoline-2-carboxamide, 4-[(4-cyano-4-pyrimidin-4-ylpiperidin-1-yl)methyl]8-fluoro-N-[(1S,2S)-2-hydroxycyclohexyl]quinoline-2-carboxamide,
8-fluoro-4-[(4-fluoro-4-pyridin-2-ylpiperidin-1-yl)methyl]-N-[(1S,2S)-2-hydroxycyclohexyl]quinline-2-carboxamide,
4-[(4-cyano-4-pyridazin-4-ylpiperidin-1-yl)methyl]-8-fluoro-N-[(1S,2S)-2-hydroxycyclohexyl]quinoline-2-carboxamide,
4-(3',6'-dihydro-2,4'-bipyridin-1'(2'H)-ylmethyl)-8-fluoro-N-[(1S,2S)-2-hydroxycyclohexyl]quinoline-2-carboxamide,
8-fluoro-N-[(1S,2S)-2-hydroxycyclohexyl]-4-({5-[4-(trifluoromethyl)phenyl]piperidin-1-yl}methyl)quinoline-2-carboxamide,
8-fluoro-N-[(1S,2S)-2-hydroxycyclohexyl]-4-[(4-pyridin-4-ylpiperidin-1-yl)methyl]quinoline-2-carboxamide,
8-fluoro-N-[(1S,2S)-2-hydroxycyclohexyl]-4-[(4-phenylpiperidin-1-yl)methyl]quinoline-2-carboxamide,
4-[(4-cyano-4-ylpiperidin-1-yl)methyl]-8-fluoro-N-[(1S,2S)-2-hydroxycyclohexyl]quinoline-2-carboxamide,
8-fluoro-N-[(1S,2S)-2-hydroxycyclohexyl]-4-[(4-pyridin-3-ylpiperidin-1-yl)methyl]quinoline-2-carboxamide,
4-[(4-cyano-3-ylpiperidin-1-yl)methyl]-8-fluoro-N-[(1S,2S)-2-hydroxycyclohexyl]quinoline-2-carboxamide,
8-fluoro-N-[(1S,2S)-2-hydroxycyclohexyl]-4-[(4-pyridin-2-ylpiperidin-1-yl)methyl]quinoline-2-carboxamide,
4-[(4-cyano-4-fluoropiperidin-1-yl)methyl]-8-fluoro-N-[(1S,2S)-2-hydroxycyclohexyl]quinoline-2-carboxamide,
4-[(4-cyano-4-fluoropiperidin-1-yl)methyl]-5,8-difluoro-N-[(1S,2S)-2-hydroxycyclohexyl]quinoline-2-carboxamide,
4-{[4-cyano-4-(4-methylpyridin-2-yl]methyl}-8-fluoro-N-[(1S,2S)-2-hydroxycyclohexyl]quinoline-2-carboxamide,
4-{[4-cyano-4-(4-methylpyridin-2-yl]methyl}-5,8-difluoro-N-[(1S,2S)-2-hydroxycyclohexyl]quinoline-2-carboxamide,
4-{[4-(4-chloropyridin-2-yl)-4-fluoropiperidin-1-yl]methyl}-8-fluoro-N-[(1S,2S)-2-hydroxycyclohexyl]quinoline-2-carboxamide,
8-fluoro-4-{[4-fluoro-4-(4-methylpyridin-2-yl)piperidin-1-yl]methyl}-N-[(1S,2S)-2-hydroxycyclohexyl]quinoline-2-carboxamide,
and pharmaceutically acceptable salts thereof.

13. A pharmaceutical composition comprising a therapeutically effective amount of a compound of claim 1, or a pharmaceutically acceptable salt thereof, and a pharmaceutically acceptable carrier.

14. A pharmaceutical composition for the treatment of a disease or disorder mediated by the muscarinic M1 receptor, wherein said disease or disorder is selected from the group consisting of Alzheimer's disease, schizophrenia, pain or sleep disorders, comprising a therapeutically effective amount of a compound of claim 1, or a pharmaceutically acceptable salt thereof, and a pharmaceutically acceptable carrier.

15. A method of treating a disease or disorder mediated by the muscarinic M1 receptor, wherein said disease or disorder is selected from the group consisting of Alzheimer's disease, schizophrenia, pain or sleep disorders in a patient in need thereof, comprising administering to the patient a therapeutically effective amount of a compound of claim 1, or a pharmaceutically acceptable salt thereof, and a pharmaceutically acceptable carrier.

* * * * *